United States Patent
Hanssen et al.

(10) Patent No.: US 7,375,109 B2
(45) Date of Patent: May 20, 2008

(54) GLYCINE-SUBSTITUTED THIENO[2,3-D]PYRIMIDINES WITH COMBINED LH AND FSH AGONISTIC ACTIVITY

(75) Inventors: Robert Gerardus Jules Marie Hanssen, BH Oss (NL); Cornelis Marius Timmers, BH Oss (NL); Jan Kelder, BH Oss (NL)

(73) Assignee: N.V. Organon, Oss (NL)

( * ) Notice: Subject to any disclaimer, the term of this patent is extended or adjusted under 35 U.S.C. 154(b) by 275 days.

(21) Appl. No.: 10/488,483

(22) PCT Filed: Aug. 29, 2002

(86) PCT No.: PCT/EP02/09648

§ 371 (c)(1),
(2), (4) Date: Feb. 26, 2004

(87) PCT Pub. No.: WO03/020727

PCT Pub. Date: Mar. 13, 2003

(65) Prior Publication Data

US 2004/0180907 A1 Sep. 16, 2004

(30) Foreign Application Priority Data

Sep. 4, 2001 (EP) .................................. 01203328

(51) Int. Cl.
*C07D 495/04* (2006.01)
*A61K 31/519* (2006.01)
*A61P 5/08* (2006.01)

(52) U.S. Cl. ..................... 514/260.1; 544/278
(58) Field of Classification Search ................ 544/278; 514/260.1
See application file for complete search history.

(56) References Cited

FOREIGN PATENT DOCUMENTS

EP 303306 3/1993
WO 0061586 10/2000

OTHER PUBLICATIONS

Polymorphism in Pharmaceutical Solids, vol. 95, Chapter 5 entitled: Generalizatio of Pol ymorphs, Hydrates, Solvates and Amorphous Solid, pp. 202-208, 1999, Ed. Harry G. Brittan, Marcek Dekkcr, inc., New York.*
Abd-Elfattah et al., "Reactions With α-Substituted Cinnamonitriles," *Tetrahedron* 39 (1983) 3197-3199.
Abdel-Hady et al., "Syntheses of Some Thieno[2,3-d]Pyrimidines," *Sulfur Lett.* 9 (1989) 101-108.
Carabateas et al., "1-Ethyl-1,4-dihydro-4-oxo-7-(pyridinyl)-3-quinolinecarboxylic Acids. I. Synthesis of 3- and 4-(3-Aminophenyl)pyridine Intermediates," *J. Heterocyclic Chem.* 21 (1984) 1849-1856.

Dorrington et al, "Effects of FSH on Gonadal Functions," *Recent Prog. Horm. Res.* 35 (1979) 301-342.
Heilbron et al., "Arylpyridines. Part IV. 3- and 4-Pyridyldiphenyls," *J. Chem. Soc.* (1940) 1279-1284.
Hussain et al., "A One Step Synthesis of 2-Methylthio-6-oxopyrimidine Derivatives: Preparation of Fused Pyrimidinones," *J. Heterocyclic Chem.* 22 (1985) 169-171.
Insler, V., "Gonadotropin Therapy: New Trends and Insights," *Int. J. Fertil.* 33 (1988) 85-97.
Jia et al., "Expression of Human Luteinizing Hormone (LH) Receptor; Interaction with LH and Chorionic Gonadotropin from Human but not Equine, Rat, and Ovine Species," *Mol. Endo.* 5 (1991) 759-768.
Kambe et al., "A One-Step Synthesis of 4-Oxo-2-thioxopyrimidine Derivatives by the Ternary Condensation of Ethyl Cyanoacetate, Aldehydes, and Thiourea," *Synthesis* (1979) 287-289.

(Continued)

*Primary Examiner*—Brenda L. Coleman
*Assistant Examiner*—Susanna Moore
(74) *Attorney, Agent, or Firm*—Susan Hess

(57) ABSTRACT

The present invention resides in glycine substituted thieno[2,3-d]pyrimidine derivatives according to general formula I, (Formula I)

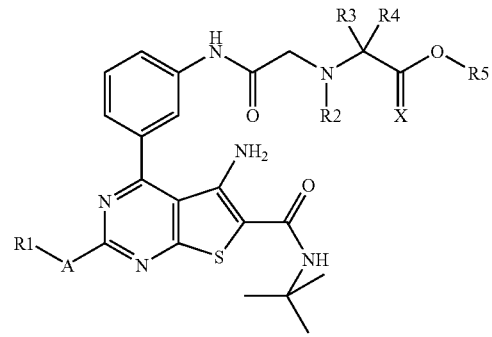

or a pharmaceutically acceptable salt thereof, wherein
X is O or H,H
A is S, NH, N($R^6$), O or a bond;
$R^1$ is (1-4C)alkyl, (2-4C)alkenyl, phenyl or (2-5C)heteroaryl, the phenyl or heteroaryl ring optionally being substituted with one or more of the group of substituents: hydroxy, halogen, nitro, trifluoromethyl, cyano, amino or (1-4C)(di)alkylamino and
$R^2$ is H, (1-4C)alkyl, (1-4C)alkoxy(2-4C)alkyl or hydroxy(2-4C)alkyl;
$R^3$ and $R^4$ can be independently selected from H and hydroxy(1-4C)alkyl;
$R^5$ is H or (1-4C)alkyl;
$R^6$ can be selected from the same groups as described for $R^1$.

The compounds of the invention have LH as well as FSH receptor activating activity and can be used in fertility regulating therapies.

12 Claims, No Drawings

OTHER PUBLICATIONS

Lévy et al., "The Role of LH in Ovarian Stimulation," *Human Reproduction* 15 (2000) 2258-2265.

Lu et al., "Effects of amphotericin B and ketoconazole on mouse oocyte maturation: implications on the role of meiosis-activating sterol," *Mol. Cell Endocrinol.* 164 (2000) 191-196.

Mannaerts et al., "Applications of In Vitro Bioassays for Gonadotrophins," Neuro-endocrinology of Reproduction. Ed. R. Rolland et al. (1987) 49-58.

Morse et al., Heterogeneity of Proteins in Commercial Preparations of Human Chorionic Gonadotropin (hCG) Demonstrated by Western Blotting, *Amer. J. Reproduct. Immunol. And Microbiology* 17 (1988) 134-140.

Navot et al., "The Use of Follicle-Stimulating Hormone for Controlled Ovarian Hyperstimulation in in Vitro Fertilization," *J. In Vitro Fert. Embryo Transfer* 5 (1988) 3-13.

Nayudu, et al., "Factors Influencing the Rate of Preantral and Antral Growth of Mouse Ovarian Follicles in vitro," *J. Reprod. Fert.* 95 (1992) 349-362.

Santilli et al., "Thieno[2,3-*d*]pyrimidines. I. A New Method for the Preparation of Esters and Amides of Thieno[2,3-*d*]pyrimidine-6-carboxylic Acids," *J. Heterocyclic Chem.* 8 (1971) 445-453.

Sharp, R.M., "Intratesticular Control of Steroidogenesis," *Clin. Endocrinol.* 33 (1990) 787-807.

Stratowa, et al., "Use of a Luciferase Reporter System for Characterizing G-Protein-Linked Receptors," *Curr. Opin. Biotech.* 6 (1995) 574-581.

Tumkevičius, S., "A Facile Synthesis of 5*H*-1-Thia-3,5,6,8-tetraazaacenaphthylenes," *Liebigs. Ann.* 9 (1995) 1703-1705.

Van Damme et al., "An Improved in Vitro Bioassay Method for Measuring Luteinizing Hormone (LH) Activity Using Mouse Leydig Cell Preparations," *Acta Endocrinol.* 77 (1974) 655-671.

\* cited by examiner

GLYCINE-SUBSTITUTED THIENO[2,3-D]PYRIMIDINES WITH COMBINED LH AND FSH AGONISTIC ACTIVITY

The invention relates to compounds having glycoprotein hormone agonistic activity, in particular to compounds having both Luteinizing Hormone (LH) and Follicle Stimulating Hormone (FSH) agonistic activity. The invention furthermore relates to pharmaceutical compositions containing the same as well as to the use of these compounds in medical therapy, particularly for use as a control of fertility.

Gonadotropins serve important functions in a variety of bodily functions including metabolism, temperature regulation and the reproductive process. The hypophyseal gonadotropins FSH and LH for example play a pivotal role in the stimulation of follicle development and maturation whereas LH is involved in induction of the ovulatory process (Sharp, R. M. Clin. Endocrinol 33:787-807, 1990; Dorrington and Armstrong, Recent Prog. Horm. Res 35: 301-342, 1979; Levy et al, Human Reproduction 15:2258-2265, 2000).

Currently, LH is applied clinically, in combination with FSH, for ovarian stimulation i.e. ovarian hyperstimulation for in vitro fertilisation (IVF) and induction of ovulation in infertile anovulatory women (Insler, V., Int. J. Fertility 33:85-97, 1988, Navot and Rosenwaks, J. Vitro Fert. Embryo Transfer 5:3-13, 1988), as well as for male hypogonadism and male infertility.

Gonadotropins act on specific gonadal cell types to initiate ovarian and testicular differentiation and steroidogenesis. The actions of these pituitary and placental hormones are mediated by specific plasma membrane receptors that are members of the large family of G-protein coupled receptors. They consist of a single polypeptide with seven transmembrane domains and are able to interact with the Gs protein, leading to the activation of adenyl cyclase.

Gonadotropins destined for therapeutic purposes can be isolated from human urine sources and are of low purity (Morse et al, Amer. J. Reproduct. Immunol. and Microbiology 17:143, 1988). Alternatively, they can be prepared as recombinant gonadotropins. In addition to these proteins, gonadotropin receptors can be activated or deactivated by synthetic low molecular weight compounds. Bicyclic heteroaromatic compounds have been described in WO 00/61586. By in vitro and in vivo experiments they are shown to be useful as LH agonists.

In normal females the release of pituitary LH and FSH is characterized by a mid-cycle surge which precedes the ovulation. Ovulation is characterized by three distinct physiological phenomena i.e. oocyte maturation, follicular rupture and luteinization. While the role of the LH-surge in the in vivo induction of these phenomena is undisputed, the role of the FSH-surge is less clear. However, it has been shown recently that FSH induces oocyte maturation in vitro by inducing cumulus cells to produce a factor that positively overcomes hypoxanthine induced meiotic arrest (Lu et al, Mol. Cell. Endocrinol. 164:191-196, 2000). This factor is thought to be a meiosis activating sterol (MAS).

The present invention provides low molecular weight compounds that show LH activity. In addition to LH activity unexpectedly they also have FSH activity. In general these compounds are thieno[2,3-d]pyrimidines which at the 4-position of the pyrimidine ring are substituted by a phenyl group which in turn is substituted at the meta position. This substituent comprises a three-atom spacer (NH—C(O)—CH$_2$), which is further functionalized with a substituted amino group. Generally the compounds have FSH agonistic activity in varying degrees but typically less than the LH agonistic activity.

The present invention resides in glycine substituted thieno[2,3-d]pyrimidine derivatives according to general formula I,

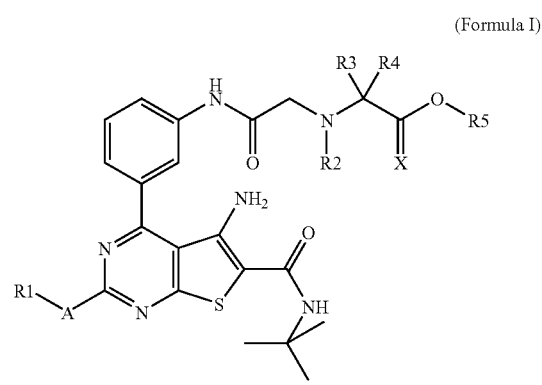

(Formula I)

or a pharmaceutically acceptable salt thereof, wherein
X is O or H,H
A is S, NH, N(R$^6$), O or a bond;
R$^1$ is (1-4C)alkyl, (2-4C)alkenyl, phenyl or (2-5C)heteroaryl, the phenyl or heteroaryl ring optionally being substituted with one or more of the group of substituents: hydroxy, halogen, nitro, trifluoromethyl, cyano, amino or (1-4C)(di)alkylamino and
R$^2$ is H, (1-4C)alkyl, (1-4C)alkoxy(2-4C)alkyl or hydroxy(2-4C)alkyl;
R$^3$ and R$^4$ can be independently selected from H, (1-4C)alkyl and hydroxy(1-4C)alkyl;
R$^5$ is H or (1-4C)alkyl.
R$^6$ can be selected from the same groups as described for R$^1$.

The term (1-4C)alkyl as used in the definition of formula I means a branched or unbranched alkyl group having 1-4 carbon atoms, being methyl, ethyl, n-propyl, isopropyl, n-butyl, sec-butyl or tert-butyl.

The term (2-4C)alkenyl as used in the definition of formula I means a branched or unbranched alkenyl group having 2-4 carbon atoms, being vinyl, 1-propenyl, 2-propenyl, 1-methyl-vinyl, 1-butenyl, 2-butenyl, 3-butenyl, 2-methyl-1-propenyl, 2-methyl-2-propenyl, 1-methyl-1-propenyl, 1-ethyl-vinyl.

The term (1-4C)alkoxy(1-4C)alkyl means an alkyl group having 1-4 carbon atoms, attached via an oxygen atom to another alkyl group having 1-4 carbon atoms, the alkyl moieties having the same meaning as previously defined.

The term (1-4C)alkoxy(2-4C)alkyl means an alkyl group having 1-4 carbon atoms, attached via an oxygen atom to another alkyl group having 2-4 carbon atoms, the alkyl moieties having the same meaning as previously defined.

The term hydroxy(1-4C)alkyl means an hydroxyl group attached to an alkyl group having 1-4 carbon atoms, the alkyl moiety having the same meaning as previously defined.

The term hydroxy(2-4C)alkyl means an hydroxyl group attached to an alkyl group having 2-4 carbon atoms, the alkyl moiety having the same meaning as previously defined.

The term (1-4C)(di)alkylamino means one or two alkyl groups having 1-4 carbon atoms as previously defined, attached to a nitrogen atom.

The term (2-5C)heteroaryl means an, optionally substituted, aromatic group having 2-5 carbon atoms, at least including one heteroatom selected from N, O and/or S, like imidazolyl, thienyl, furyl or pyridyl.

The term halogen means fluorine, chlorine, bromine or iodine.

It has been shown that compounds of the above mentioned formula I show agonistic LH and FSH activity. In an in vitro bioassay using CHO cells stably transfected with the human LH or FSH receptor, respectively, the $EC_{50}$ with regard to the LH receptor was found to be less than $5.10^{-8}$ M whereas with regard to the FSH receptor the $EC_{50}$ was less than $10^{-5}$M. Typically the FSH activity ranges from an activity of about 0.1% of the LH agonist stimulation to about 10% of the LH agonist stimulation.

The invention further resides in a pharmaceutical composition comprising a thieno[2,3-d]pyrimidine derivative compound or salts thereof having the general formula I.

Thus, the compounds according to the invention can be used in therapy. A further aspect of the invention resides in the use of a thieno[2,3-d]pyrimidine compound having the general formula I for the manufacture of a medicament for the control of fertility, more preferably induction of ovulation. The present compounds are used to activate both the LH and FSH receptors. The compound of the present invention can be used therefore in a method to treat females with fertility problems.

The thieno[2,3-d]pyrimidine compounds of this invention may possess one or more chiral carbon atoms. The compounds may therefore be obtained as chirally pure compounds or as a mixture of diastereomers and/or enantiomers. Methods for obtaining the chirally pure compounds are well known in the art, e.g. crystallization or chromatography.

For therapeutic use, salts of the compounds of formula I are those wherein the counterion is pharmaceutically acceptable. However, acid addition salts of bases according to formula I, may also find use, for example, in the preparation or purification of a pharmaceutically acceptable compound. All salts, whether pharmaceutically acceptable or not, are included within the ambit of the present invention.

Examples of acid addition salts include those derived from mineral acids such as hydrochloric acid, phosphoric acid, sulphuric acid, preferably hydrochloric acid, and organic acids like citric acid, tartaric acid, acetic acid, lactic acid, maleic acid, malonic acid, fumaric acid, glycolic acid, succinic acid, and the like.

Suitable administration routes for the compounds of formula I or pharmaceutically acceptable salts thereof, also referred to herein as the active ingredient are intramuscular injections, subcutaneous injections, intravenous injections or intraperitoneal injections, oral and intranasal administration. Preferably, the compounds may be administered orally. The exact dose and regimen of administration of the active ingredient, or a pharmaceutical composition thereof, will necessarily be dependent upon the therapeutic effect to be achieved (treatment of infertility; contraception), and may vary with the particular compound, the route of administration, and the age and condition of the individual subject to whom the medicament is to be administered.

In general, parenteral administration requires lower dosages than other methods of administration which are more dependent upon adsorption. However, a dosage for humans preferably contains 0.0001-25 mg per kg body weight. The desired dose may be presented as one dose or as multiple subdoses administered at appropriate intervals throughout the day. In case of female recipients, doses may be administered at appropriate daily intervals throughout the menstrual cycle for follicular support or as a single dose for ovulation induction. The dosage as well as the regimen of administration may differ between a female and a male recipient.

In case of in vitro or ex vivo applications, like in IVF applications, the compounds of the inventions are to be used in the incubation media in a concentration of approximately 0.01-5 μg/ml.

The present invention thus also relates to pharmaceutical compositions comprising a thieno[2,3-d]pyrimidine compound according to formula I in admixture with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for oral, rectal nasal, topical (including transdermal, buccal and sublingual), vaginal or parenteral (including subcutaneous, intramuscular, intravenous and intradermal) administration. The compositions may be prepared by any method well known in the art of pharmacy, for example, using methods such as those described in Gennaro et al., Remington's Pharmaceutical Sciences (18th ed., Mack Publishing company, 1990, see especially Part 8: *Pharmaceutical Preparations and Their Manufacture*).

Such methods include the step of bringing in association the active ingredient with any auxiliary agent. The auxiliary agent(s), also named accessory ingredients, include those conventional in the art (Gennaro, supra), such as, fillers, binders, diluents, disintegrants, lubricants, colorants, flavoring agents and wetting agents.

Pharmaceutical compositions suitable for oral administration may be presented as discrete dosage units such as pills, tablets or capsules, or as a powder or granules, or as a solution or suspension. The active ingredient may also be presented as a bolus or paste.

The compositions can further be processed into a suppository or enema for rectal administration.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example, water prior to use.

Compositions, or formulations, suitable for administration by nasal inhalation include fine dusts or mists which may be generated by means of metered dose pressurized aerosols, nebulisers or insufflators.

The thieno[2,3-d]pyrimidine compounds of the invention can also be administered in the form of implantable pharmaceutical devices, consisting of a core of active material, encased by a release rate-regulating membrane. Such implants are to be applied subcutaneously or locally, and will release the active ingredient at an approximately constant rate over relatively large periods of time, for instance from weeks to years. Methods for the preparation of implantable pharmaceutical devices as such are known in the art, for example as described in European Patent 0,303,306 (AKZO N.V.).

Thus, the compounds according to the present invention can be used for the same clinical purposes as the native LH, with the advantage that they possess FSH activity, display altered stability properties and can be administered differently.

The compounds of the present invention, represented by formula (I) can generally be prepared by nucleophilic substitution of compounds of general formula (II) wherein Q=Cl or Br with amines of general formula (III) in an appropriate solvent such as N,N-dimethylformamide or THF at room temperature in the presence of a tertiary base such as N,N-diisopropylethylamine. Many amines of general formula (III) are commercially available.

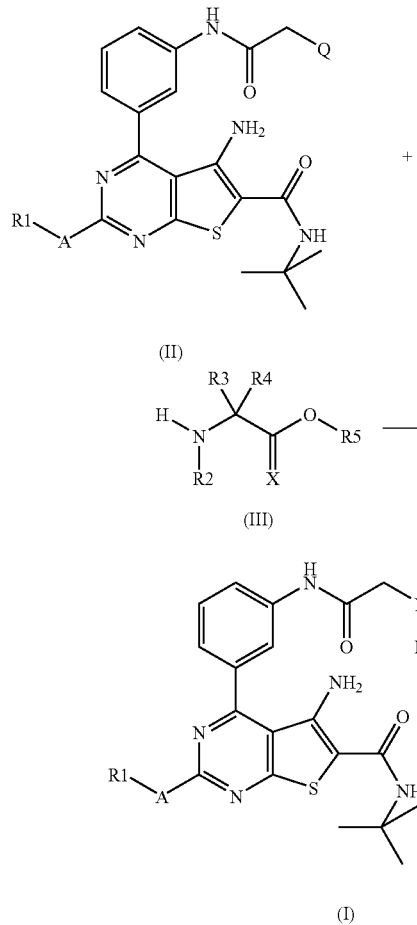

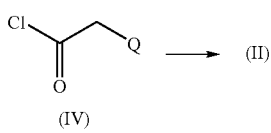

Compounds of formula (V) are accessible by art-known reduction of the nitro function in derivatives of formula (VI), using an appropriate reducing agent such as hydrogen in the presence of a metal (Pd/Pt) catalyst. Related reductions have been described in: P. M. Carabateas, P. R. Brundage, K. O. Gelotte, M. D. Gruett, R. R. Lorenz, J. Heterocycl. Chem. 21, 1849 (1984). Alternatively, the reduction can be effected with tin(II) chloride in a protic solvent such as ethanol in the presence of hydrochloric acid at elevated temperature (J. Heilbron, J. Chem. Soc, 1279 (1940)).

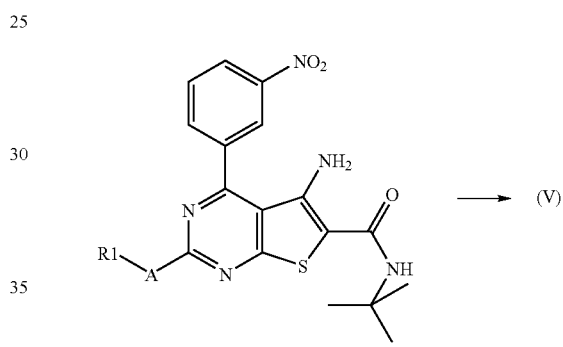

Thienopyrimidines of general formula (VI) are accessible by condensation of carboxylic acids (VII) with tert-butyl amine under the influence of a coupling agent such as O-(benzotriazol-1-yl)-N,N,N',N'-tetramethyluronium tetrafluoroborate (TBTU) or bromotripyrrolidinophosphonium hexafluorophosphate (PyBrOP) and a tertiary base, e.g. N,N-diisopropylethylamine.

Derivatives of formula (II) wherein Q=Cl or Br can be prepared by regioselective acylation of meta aniline derivatives of formula (V-a) with acyl chlorides of type (IV), wherein Q=Cl or Br in the presence of a tertiary base such as N,N-diisopropylethylamine in a suitable solvent such as dichloromethane or THF.

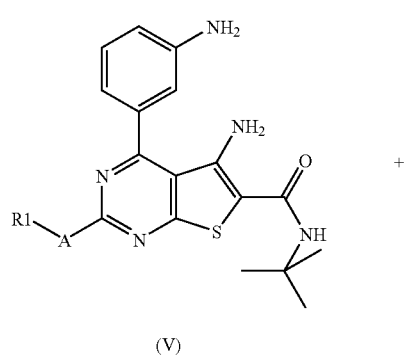

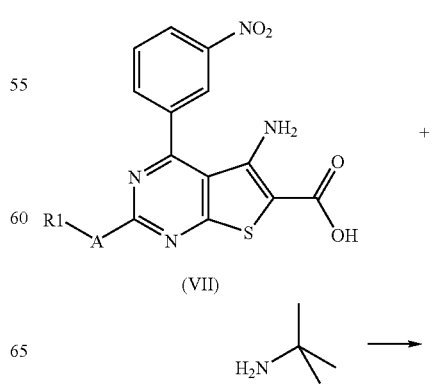

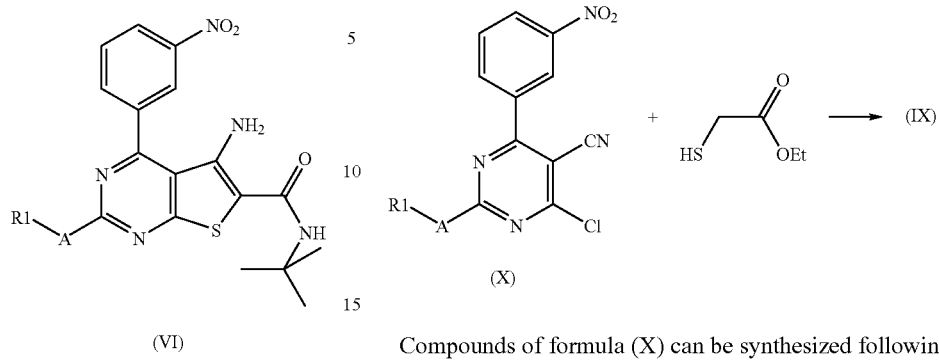

(VI)

Saponification of the corresponding ethyl esters (VIII) to carboxylic acids (VII) takes place in the presence of a base such as lithium hydroxide, potassium hydroxide or sodium hydroxide in aqueous dioxane at elevated temperature (80° C. to reflux).

Compounds of formula (X) can be synthesized following literature procedures as described for example by A. A. Santilli, D. H. Kim and S. V. Wanser, J. Heterocycl. Chem. 8, 445, 1971. In a typical experiment, an amide of general structure (XI) is treated with $POCl_3$ at elevated temperature (80° C. to reflux). The addition of an appropriate solvent, e.g. dioxane, and/or the addition of either $PCl_5$ or N,N-dimethylaniline to the reaction mixture may result in shorter reaction times and higher yields of chlorides (X).

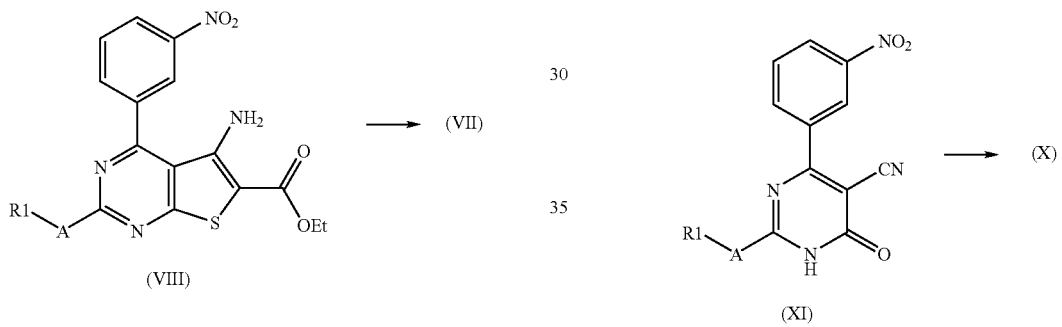

Bicyclic systems of general formula (VIII) are formed by substitution of chlorides of formula (X) with ethyl mercaptoacetate under the agency of N,N-diisopropylethylamine, followed by base-catalyzed ring-closure of the intermediate thioethers (IX). This type of thieno[2,3-d]pyrimidine ring formations has been described in: S. A. Abdel-Hady, M. A. Badawy, Y. A. Ibrahim, Sulfur Left. 9, 101 (1989) and S. Tumkevicius, Liebigs Ann., 1703 (1995).

A general route towards lactams of formula (XI) comprises condensation of ethyl cyanoacetate with 3-nitrobenzaldehyde and compounds (XII), which may be isothiourea (XII-a), isourea (XII-b), monosubstituted guanidines (XII-c), disubstituted guanidines (XII-d) or amidines (XII-e).

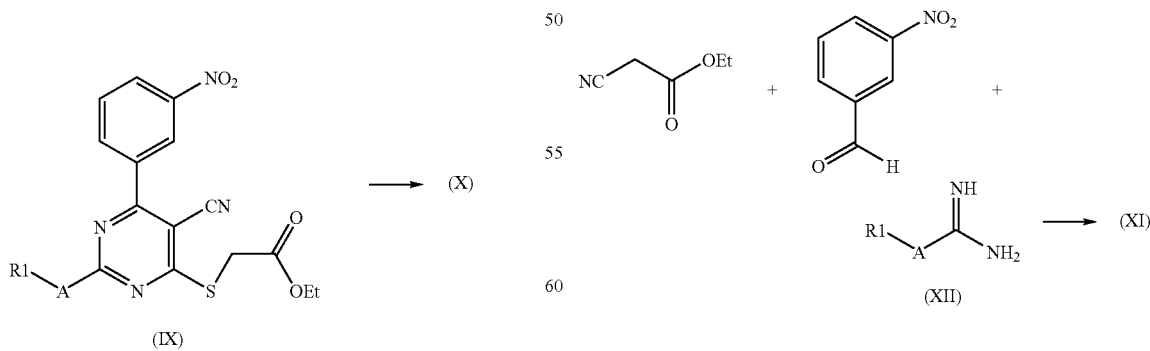

Suitable conditions for the cyclization reaction are sodium ethoxide in ethanol or N,N-diisopropylethylamine in toluene/ethanol (1/1, v/v) at reflux temperature.

In a typical experiment, ethyl cyanoacetate, 3-nitrobenzaldehyde and derivative (XII) are suspended in an appropriate solvent, e.g. ethanol, methanol, N,N-dimethylformamide, N-methylpyrrolidinone, tetrahydrofuran or pyridine and a base such as potassium carbonate, sodium acetate, sodium methoxide or sodium ethoxide is added. Reaction takes place at elevated temperature (70° C. to reflux). After filtration, residues are taken up in water and acidified (pH 2) after which products (XI) precipitate (S. Kambe, K. Saito and H. Kishi, Synthesis, 287 (1979); A. M. Abd-Elfattah, S. M. Hussain and A. M. El-Reedy, Tetrahedron 39, 3197 (1983); S. M. Hussain, A. A. El-Barbary and S. A. Mansour, J. Heterocycl. Chem. 22, 169 (1985)).

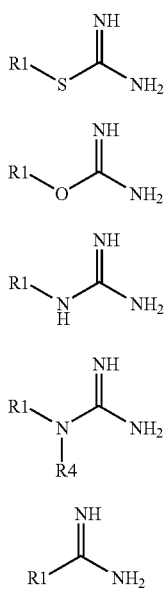

Alternatively, the compounds of the present invention wherein A=N, represented by formula (I-a), can be prepared from sulfoxide derivatives of general formula (XIII) via nucleophilic substitution with amine nucleophiles of general structure (XIV). The reaction is typically conducted at elevated temperature in the presence of a tertiary base such as N,N-diisopropylethylamine in an appropriate solvent such as 1,4-dioxane.

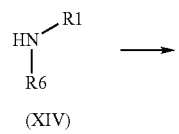

Similarly, compounds of the present invention wherein A=O, represented by formula (I-b), can be prepared from sulfoxide derivatives of general formula (XIII) via nucleophilic substitution with alkoxide nucleophiles of general structure (XV). The reaction is carried out in the presence of potassium tert-butoxide with an excess of alcohol $R^1$—OH.

The sulfoxide derivatives of general formula (XIII) are accessible by oxidation of compounds of general formula (I), wherein $R^1$=Me and A=S, represented by formula (I-c). The oxidation is effected by 3-chloroperbenzoic acid in trifluoroacetic acid. The acidic nature of the solvent prevents oxidation of the 5-amino group to the corresponding 5-nitroso derivative.

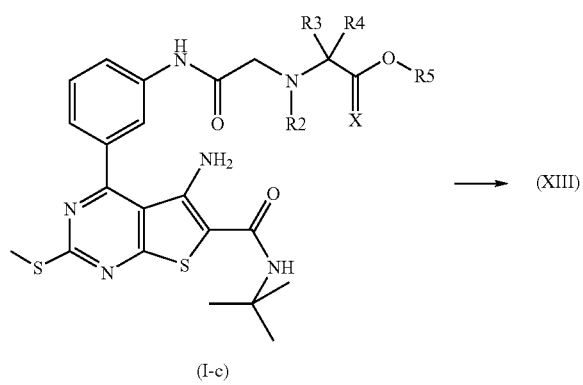

Methods to determine receptor binding as well as in vitro and in vivo assays to determine biological activity of gonadotropins are well known. In general, expressed receptor is contacted with the compound to be tested and binding or stimulation or inhibition of a functional response is measured.

To measure a functional response isolated DNA encoding the LH or the FSH receptor gene, preferably the human receptor, is expressed in suitable host cells. Such a cell might be the Chinese Hamster Ovary cell, but other cells are also suitable. Preferably the cells are of mammalian origin (Jia et al, Mol. Endocrin., 5:759-776, 1991.

Methods to construct recombinant LH or FSH expressing cell lines are well known in the art (Sambrook et al., Molecular Cloning: a Laboratory Manual, Cold Spring Harbor Laboratory Press, Cold Spring Harbor, latest edition). Expression of receptor is attained by expression of the DNA encoding the desired protein. Techniques for site directed mutagenesis, ligation of additional sequences, PCR, and construction of suitable expression systems are all, by now, well known in the art. Portions or all of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available which are compatible with a wide variety of hosts, including prokaryotic hosts such as bacteria and eukaryotic hosts such as yeast, plant cells, insect cells, mammalian cells, avian cells and the like.

Cells expressing the receptor are then contacted with the test compound to observe binding, or stimulation or inhibition of a functional response.

Alternatively isolated cell membranes containing the expressed receptor may be used to measure binding of compound.

For measurement of binding radioactively or fluorescently labeled compounds may be used. As reference compound human recombinant LH or FSH can be used. In the alternative also competition binding assays can be performed.

Another assay involves screening for LH or FSH receptor agonist compounds by determining stimulation of receptor mediated cAMP accumulation. Thus, such a method involves expression of the receptor on the cell surface of a host cell and exposing the cell to the test compound. The amount of cAMP is than measured. The level of cAMP will be reduced or increased, depending on the inhibitory or stimulating effect of the test compound upon binding to the receptor.

In addition to direct measurement of e.g. cAMP levels in the exposed cell, cells can be used which in addition to transfection with receptor encoding DNA are also transfected with a second DNA encoding a reporter gene the expression of which responds to the level of cAMP. Such reporter genes might be cAMP inducible or might be constructed in such a way that they are connected to novel cAMP responsive elements. In general, reporter gene expression might be controlled by any response element reacting to changing levels of cAMP. Suitable reporter genes are e.g. LacZ, alkaline phosphatase, firefly luciferase and green fluorescence protein. The principles of such transactivation assays are well known in the art and are described e.g. in Stratowa, Ch, Himmler, A and Czernilofsky, A. P. (1995) Curr.Opin.Biotechnol.6:574.

For selecting active compounds on the LH or FSH receptor, testing at $10^{-5}$ M must result in an activity of more than 20% of the maximal activity when LH or FSH is used as a reference. Another criterion might be the $EC_{50}$ value, which must be $<10^{-5}$ M, preferably $<10^{-7}$ M.

The skilled artisan will recognize that desirable $EC_{50}$ values are dependent on the compound tested. For example, a compound with an $EC_{50}$, which is less than 10-5 M is generally, considered a candidate for drug selection. Preferably this value is lower than $10^{-7}$ M. However, a compound which has a higher $EC_{50}$, but is selective for the particular receptor, may be even a better candidate.

Screening for LH receptor agonistic compounds can also be performed by using a mouse Leydig cell bioassay (Van Damme, M., Robersen, D. and Diczfalusy, E. (1974). Acta Endocrinol. 77: 655-671 Mannaerts, B., Kloosterboer, H. and Schuurs, A. (1987). Neuroendocrinology of reproduction. R. Rolland et al. Eds., Elsevier Science Publishers B.V., 49-58). In this assay, stimulation of LH receptor mediated testosterone production can be measured in Leydig cells isolated from male mice.

FSH agonistic activity of compounds can also be determined in an ex vivo model using cultured mouse follicles according to Nayudu, P. and Osborn, S. (1992, J. Reproduction and Fertility 95:349-362). Therefore, mouse ovarian follicles are isolated and cultured in the presence of FSH agonistic compounds to induce follicular growth. Measurements of follicular diameter and estradiol in the culture medium are indicative for follicular growth.

To measure LH in vivo activity of compounds, ovulation induction in immature mice can be studied. In this assay immature female mice are primed with urinary FSH and approximately 48 hours later treated with a LH agonistic compound. The animals are killed after LH agonist treatment and the number of ova in the oviduct is microscopically assessed.

To measure FSH in vivo activity of compounds immature female rats are treated at 0, 8, 24 and 32 hours with a FSH agonistic compound to induce follicular growth. At 52 hours after the start of the experiment the animals are injected with hCG to induce ovulation. The animals are killed 72 hours after the start of the experiment and the number of ova in the oviduct is microscopically assessed. In addition ovarian weight is determined.

The compounds of the present invention can be applied clinically in those regimens where now LH or hCG is used. These include LH substitution among subjects with hypogonadal hypogonadism either male or female, midcycle administration to induce ovulation (ovulation induction (OI) or controlled hyperstimulation (COH) or stimulation of the corpus luteum.

The following examples are illustrative for the invention and should in no way be interpreted as limiting the scope of the invention.

EXAMPLES

Example 1 tert-Butyl 5-amino-2-methylthio-4-(3-((N-methyl-N-(2-hydroxyethyl)-glycinyl)-amino)-phenyl)-thieno[2,3-d]pyrimidine-6-carboxamide (a). 5-Cyano-4-(3-nitrophenyl)-2-methylthio-6-hydroxy-pyrimidine A mixture of S-methylisothiourea sulfate (69.0 g), 3-nitrobenzaldehyde (75.0 g), ethyl cyanoacetate (56.0 ml) and potassium carbonate (72.5 g) in abs. EtOH (1500 ml) was stirred at 60° C. for 16 h. The reaction mixture was cooled to 0° C. in an ice bath. The resulting precipitate was filtered off, washed with abs. EtOH and dissolved in hot water (100° C.). The solution was cooled to room temperature, acidified with 2N HCl to pH 2 and cooled to 0° C. in an ice bath. The resulting precipitate was filtered off and washed with ice water. Residual water in the precipitate was removed by coevaporation with 1,4-dioxane.

Yield: 54.0 g. MS-ESI: $[M+H]^+$=289.0 TLC: $R_f$=0.3, silica gel, DCM/MeOH=9/1 (v/v).

(b). 6-Chloro-5-cyano-4-(3-nitrophenyl)-2-methylthio-pyrimidine $POCl_3$ (100 ml) was added to a stirred solution of 5-cyano-4-(3-nitrophenyl)-2-methylthio-6-hydroxy-pyrimidine (example 1(a), 25.0 g) in dry 1,4-dioxane (300 ml). After 3 h at 90° C., the mixture was cooled to room temperature and concentrated under reduced pressure. The residue was dissolved in 1,4-dioxane (100 ml) and the resulting solution was cooled to 0° C. Ice water was cautiously added. The resulting precipitate was filtered off and washed with water. Residual water in the precipitate was removed by coevaporation with 1,4-dioxane.

Yield: 26.0 g. MS-ESI: $[M+H]^+$=307.0 TLC: $R_f$=0.5, silica gel, heptane/EtOAc=3/2 (v/v).

(c). Ethyl 5-cyano-4-(3-nitrophenyl)-2-methylthio-6-(ethoxycarbonylmethylthio)-pyrimidine DIPEA (15.7 ml) was added to a stirred solution of ethyl 2-mercaptoacetate (9.3 ml) and 6-chloro-5-cyano-4-(3-nitrophenyl)-2-methylthio-pyrimidine (example 1(b), 26.0 g) in a mixture of EtOH (250 ml) and DCM (250 ml). After 1 h at room temperature, 0.1N aq. HCl (500 ml) was added to the mixture which was then extracted with DCM (3×500 ml), dried ($MgSO_4$) and concentrated under reduced pressure.

Yield: 28.0 g MS-ESI: $[M+H]^+$=391.4 TLC: $R_f$=0.5, silica gel, heptane/EtOAc=3/2 (v/v).

(d). Ethyl 5-amino-4-(3-nitrophenyl)-2-methylthio-thieno[2,3-d]pyrimidine-6-carboxylate A mixture of ethyl 5-cyano-4-(3-nitrophenyl)-2-methylthio-6-(ethoxycarbonylmethylthio)-pyrimidine (example 1(c), 28.0 g) and DIPEA (30 ml) in a mixture of toluene (150 ml) and EtOH (150 ml) was stirred at reflux temperature (100° C.) for 16 h. The mixture was then cooled to room temperature and concentrated under reduced pressure. Residual DIPEA was removed by coevaporation with toluene.

Yield: 28.0 g MS-ESI: $[M+H]^+$=391.4 TLC: $R_f$=0.6, silica gel, heptane/EtOAc=3/2 (v/v).

(e). Ethyl 5-amino-4-(3-aminophenyl)-2-methylthio-thieno[2,3-d]pyrimidine-6-carboxylate EtOH (400 ml) was added to a mixture of ethyl 5-amino-4-(3-nitrophenyl)-2-methylthio-thieno[2,3-d]pyrimidine-6-carboxylate (example 1(d), 28.0 g), concentrated aq. HCl (15 ml) and tin (II) chloride (41.0 g) in 1,4-dioxane (400 ml). The mixture was stirred at 90° C. for 16 h. The mixture was then cooled to room temperature and concentrated under reduced pressure. The residue was suspended in EtOAc (1000 ml). 4N aq. NaOH was added to obtain a pH of 10-11. The mixture was vigourously stirred and the organic layer was separated, dried ($MgSO_4$) and concentrated under reduced pressure.

Yield: 21.0 g MS-ESI: $[M+H]^+$=361.0 TLC: $R_f$=0.6, silica gel, heptane/EtOAc=3/2 (v/v).

(f). 5-Amino-4-(3-aminophenyl)-2-methylthio-thieno[2,3-d]pyrimidine-6-carboxylic acid Potassium hydroxide (32.4 g) was added to a solution of ethyl 5-amino-4-(3-aminophenyl)-2-methylthio-thieno[2,3-d]pyrimidine-6-carboxylate (example 1(e), 21.0 g) in a mixture of 1,4-dioxane (300 ml) and water (100 ml). After 16 h at 90° C., the mixture was cooled to 10° C. and 2N aq. citric acid (300 ml) was added under vigourous stirring. The resulting precipitate was filtered off, washed with water (180 ml) and dried in vacuo.

Yield: 14.0 g MS-ESI: $[M+H]^+$=333.0 TLC: $R_f$=0.5, silica gel, DCM/MeOH=9/1 (v/v).

(g). tert-Butyl 5-amino-4-(3-aminophenyl)-2-methylthio-thieno[2,3-d]pyrimidine-6-carboxamide TBTU (16.1 g) was added to a solution of 5-amino-4-(3-aminophenyl)-2-methylthio-thieno[2,3-d]pyrimidine-6-carboxylic acid (example 1(f), 14.0 g), DIPEA (17.4 ml) and tert-butylamine (7.3 g) in DCM/DMF (1/1, v/v, 250 ml). After 3 h at room temperature, the mixture was diluted with DCM (50 ml), washed with sat. aq. $NaHCO_3$ (3×100 ml), 0.1 N aq. HCl (100 ml) and water (100 ml). The organic layer was concentrated under reduced pressure. The crude product was purified by crystallisation from warm abs. EtOH (300 ml).

Yield: 10.5 g MS-ESI: $[M+H]^+$=388.2 HPLC:$R_t$=30.72 min, Luna C-18(2), 5 μm, 250×2.0 mm, detection UV=210 nm, oven temperature=40° C., flow=0.25 ml/min, eluent water/ACN/MeOH=90/9.5/0.5 to 0/95/5, run time=50 min.

(h). tert-Butyl 5-amino-2-methylthio-4-(3-(2-bromoacetamido)-phenyl)-thieno[2,3-d]pyrimidine-6-carboxamide Bromoacetyl chloride (615 mg) was added to a solution of tert-butyl 5-amino-2-methylthio-4-(3-aminophenyl)-thieno[2,3-d]-pyrimidine-6-carboxamide (example 1(g), 1.08 g) and DIPEA (2.43 ml) in dry DCM (20 ml). After 3 h at room temperature, the mixture was diluted with DCM, washed with sat. aq. $NaHCO_3$, dried ($MgSO_4$) and concentrated under reduced pressure. The crude product was purified by chromatography on silica gel using heptane/EtOAc=3/2 (v/v) as eluent.

Yield: 910 mg MS-ESI: $[M+H]^+$=510.2 TLC: $R_f$=0.3, silica gel, heptane/EtOAc=3/2 (v/v).

(i). tert-Butyl 5-amino-2-methylthio-4-(3-((N-methyl-N-(2-hydroxyethyl)-glycinyl)-amino)-phenyl)-thieno[2,3-d]pyrimidine-6-carboxamide N-methyl-2-amino-ethanol (250 mg) was added to a solution of tert-butyl 5-amino-4-(3-(2-bromoacetamido)-phenyl)-2-methylthio-thieno[2,3-d]pyrimidine-6-carboxamide (example 1(h), 250 mg) in DCM (5 ml). After 16 h at room temperature, the mixture was diluted with DCM (50 ml), washed with sat. aq. NaHCO$_3$, dried (MgSO$_4$) and concentrated under reduced pressure. The crude product was purified by HPLC using a Luna C-18 column with the following gradient: 0.1% aq. TFA+10% aq. ACN/ACN=90/10 to 10/90 (v/v) in 30 min. The title compound was then lyophilized from a mixture of 1,4-dioxane, 0.1% aq. TFA and water.

Yield: 112 mg (TFA-salt) MS-ESI: [M+H]$^+$=503.2 HPLC: R$_t$=11.45 min, column Luna C-18(2), 3 μm, 100×2.0 mm, detection UV=210 nm, oven temperature=40° C., flow=0.25 ml/min, eluent phosphate buffer 50 mM pH 2.1/water/ACN=10/80/10 to 10/10/80 (v/v/v), run time=20 min.

Example 2 tert-Butyl 5-amino-2-methylthio-4-(3-((N-(1-hydroxy-2-methyl-prop-2-yl)-glycinyl)-amino)-phenyl)-thieno[2,3-d]pyrimidine-6-carboxamide 2-amino-2-methyl-propanol (250 mg) was added to a solution of tert-butyl 5-amino-4-(3-(2-bromoacetamido)-phenyl)-2-methylthio-thieno[2,3-d]pyrimidine-6-carboxamide (example 1(h), 250 mg) in DCM (5 ml). After 16 h at room temperature, the mixture was diluted with DCM (50 ml), washed with sat. aq. NaHCO$_3$, dried (MgSO$_4$) and concentrated under reduced pressure. The crude product was purified by HPLC using a Luna C-18 column with the following gradient: 0.1% aq. TFA+10% aq. ACN/ACN=90/10 to 10/90 (v/v) in 30 min. The title compound was then lyophilized from a mixture of 1,4-dioxane, 0.1% aq. TFA and water.

Yield: 67 mg (TFA-salt) MS-ESI: [M+H]$^+$=517.2 HPLC: R$_t$=12.67 min, column Luna C-18(2), 3 μm, 100×2.0 mm, detection UV=210 nm, oven temperature=40° C., flow=0.25 ml/min, eluent phosphate buffer 50 mM pH 2.1/water/ACN=10/80/10 to 10/10/80 (v/v/v), run time=20 min.

Example 3 tert-Butyl 5-amino-2-methylthio-4-(3-((N-(methoxycarbonylmethyl)-glycinyl)-amino)-phenyl)-thieno[2,3-d]pyrimidine-6-carboxamide Glycine methyl ester hydrochloride (200 mg) was added to a solution of tert-butyl 5-amino-4-(3-(2-bromoacetamido)-phenyl)-2-methylthio-thieno[2,3-d]pyrimidine-6-carboxamide (example 1(h), 250 mg) and N,N-diisopropylethylamine (0.20 ml) in DCM (5 ml). After 16 h at room temperature, the mixture was diluted with DCM (50 ml), washed with sat. aq. NaHCO$_3$, dried (MgSO$_4$) and concentrated under reduced pressure. The crude product was purified by TALC using a Luna C-18 column with the following gradient: 0.1% aq. TFA+10% aq. ACN/ACN=90/10 to 10/90 (v/v) in 30 min. The title compound was then lyophilized from a mixture of 1,4-dioxane, 0.1% aq. TFA and water.

Yield: 133 mg (TFA-salt) MS-ESI: [M+H]$^+$=517.2 HPLC: R$_t$=11.87 min, column Luna C-18(2), 3 μm, 100×2.0 mm, detection UV=210 nm, oven temperature=40° C., flow=0.25 ml/min, eluent phosphate buffer 50 mM pH 2.1/water/ACN=10/80/10 to 10/10/80 (v/v/v), run time=20 min.

Example 4 tert-Butyl 5-amino-2-methylthio-4-(3-((N-ethyl-N-(2-methoxyethyl)-glycinyl)-amino)-phenyl)-thieno[2,3-d]pyrimidine-6-carboxamide N-(2-methoxyethyl)-ethylamine (266 mg) was added to a solution of tert-butyl 5-amino-4-(3-(2-bromoacetamido)-phenyl)-2-methylthio-thieno[2,3-d]pyrimidine-6-carboxamide (example 1(h), 200 mg) in DCM (5 ml). After 16 h at room temperature, the mixture was diluted with DCM (50 ml), washed with sat. aq. NaHCO$_3$, dried (MgSO$_4$) and concentrated under reduced pressure. The crude product was purified by HPLC using a Luna C-18 column with the following gradient: 0.1% aq. TFA+10% aq. ACN/ACN=90/10 to 10/90 (v/v) in 30 min. The title compound was then lyophilized from a mixture of 1,4-dioxane, 0.1% aq. TFA and water.

Yield: 84 mg (TFA-salt) MS-ESI: [M+H]$^+$=531.2 HPLC: R$_t$=12.62 min, column Luna C-18(2), 3 μm, 100×2.0 mm, detection UV=210 nm, oven temperature=40° C., flow=0.25 ml/min, eluent phosphate buffer 50 mM pH 2.1/water/ACN=10/80/10 to 10/10/80 (v/v/v), run time=20 min.

Example 5 tert-Butyl 5-amino-2-methylthio-4-(3-((N-(R-1-methoxycarbonyl-2-methyl-prop-1-yl)-glycinyl)-amino 2,3-d]pyrimidine-6-carboxamide D-Valine methyl ester hydrochloride (250 mg) was added to a solution of tert-butyl 5-amino-4-(3-(2-bromoacetamido)-phenyl)-2-methylthio-thieno[2,3-d]pyrimidine-6-carboxamide (example 1(h), 250 mg) and N,N-diisopropylethylamine (0.20 ml) in DCM (5 ml). After 16 h at room temperature, the mixture was diluted with DCM (50 ml), washed with sat. aq. NaHCO$_3$, dried (MgSO$_4$) and concentrated under reduced pressure. The crude product was purified by HPLC using a Luna C-18 column with the following gradient: 0.1% aq. TFA+10% aq. ACN/ACN=90/10 to 10/90 (v/v) in 30 min. The title compound was then lyophilized from a mixture of 1,4-dioxane, 0.1% aq. TFA and water.

Yield: 77 mg (TFA-salt) MS-ESI: [M+H]$^+$=559.2 HPLC: R$_t$=13.22 min, column Luna C-18(2), 3 μm, 100×2.0 mm, detection UV=210 nm, oven temperature=40° C., flow=0.25 ml/min, eluent phosphate buffer 50 mM pH 2.1/water/ACN=10/80/10 to 10/10/80 (v/v/v), run time=20 min.

Example 6 tert-Butyl 5-amino-2-methylthio-4-(3-((N,N-bis-(2-methoxyethyl)-glycinyl)-amino)-phenyl)-thieno[2,3-d]pyrimidine-6-carboxamide N,N-bis-(2-methoxyethyl)-amine (400 mg) was added to a solution of tert-butyl 5-amino-4-(3-(2-bromoacetamido)-phenyl)-2-methylthio-thieno[2,3-d]pyrimidine-6-carboxamide (example 1(h), 250 mg) in DCM (5 ml). After 16 h at room temperature, the mixture was diluted with DCM (50 ml), washed with sat. aq. NaHCO$_3$, dried (MgSO$_4$) and concentrated under reduced pressure. The crude product was purified by HPLC using a Luna C-18 column with the following gradient: 0.1% aq. TFA+10% aq. ACN/ACN=90/10 to 10/90 (v/v) in 30 min. The title compound was then lyophilized from a mixture of 1,4-dioxane, 0.1% aq. TFA and water.

Yield: 166 mg (TFA-salt) MS-ESI: [M+H]⁺=561.3 HPLC: $R_t$=13.62 min, column Luna C-18(2), 3 µm, 100×2.0 mm, detection UV=210 nm, oven temperature=40° C., flow=0.25 ml/min, eluent phosphate buffer 50 mM pH 2.1/water/ACN=10/80/10 to 10/10/80 (v/v/v), run time=20 min.

Example 7 tert-Butyl 5-amino-2-methylthio-4-(3-((2,3-dihydroxy-prop-1-yl)-glycinyl)-amino)-phenyl)-thieno[2,3-d]pyrimidine-6-carboxamide 3-Amino-2-hydroxy-propanol (250 mg) was added to a solution of tert-butyl 5-amino-4-(3-(2-bromoacetamido)-phenyl)-2-methylthio-thieno[2,3-d]pyrimidine-6-carboxamide (example 1(h), 250 mg) in DCM (5 ml). After 16 h at room temperature, the mixture was diluted with DCM (50 ml), washed with sat. aq. NaHCO₃, dried (MgSO₄) and concentrated under reduced pressure. The crude product was purified by HPLC using a Luna C-18 column with the following gradient: 0.1% aq. TFA+10% aq. ACN/ACN=90/10 to 10/90 (v/v) in 30 min. The title compound was then lyophilized from a mixture of 1,4-dioxane, 0.1% aq. TFA and water.

Yield: 164 mg (TFA-salt) MS-ESI: [M+H]⁺=519.2 HPLC: $R_t$=12.62 min, column Luna C-18(2), 3 µm, 100×2.0 mm, detection UV=210 nm, oven temperature=40° C., flow=0.25 ml/min, eluent phosphate buffer 50 mM pH 2.1/water/ACN=10/80/10 to 10/10/80 (v/v/v), run time=20 min.

Example 8 tert-Butyl 5-amino-2-methylthio-4-(3-((1,3-dihydroxyprop-2-yl)-glycinyl)-amino)-phenyl)-thieno[2,3-d]pyrimidine-6-carboxamide 2-amino-3-hydroxy propanol (250 mg) was added to a solution of tert-butyl 5-amino-4-(3-(2-bromoacetamido)-phenyl)-2-methylthio-thieno[2,3-d]pyrimidine-6-carboxamide (example 1(h), 250 mg) in DCM (5 ml). After 16 h at room temperature, the mixture was diluted with DCM (50 ml), washed with sat. aq. NaHCO₃, dried (MgSO₄) and concentrated under reduced pressure. The crude product was purified by HPLC using a Luna C-18 column with the following gradient: 0.1% aq. TFA+10% aq. ACN/ACN=90/10 to 10/90 (v/v) in 30 min. The title compound was then lyophilized from a mixture of 1,4-dioxane, 0.1% aq. TFA and water.

Yield: 117 mg (TFA-salt) MS-ESI: [M+H]⁺=519.2 HPLC: $R_t$=12.62 min, column Luna C-18(2), 3 µm, 100×2.0 mm, detection UV=210 nm, oven temperature=40° C., flow=0.25 ml/min, eluent phosphate buffer 50 mM pH 2.1/water/ACN=10/80/10 to 10/10/80 (v/v/v), run time=20 min.

Example 9 tert-Butyl 5-amino-2-phenyl-4-(3-((N-ethyl-N-(2-hydroxyethyl)-glycinyl)-amino)-phenyl)-thieno[2,3-d]pyrimidine-6-carboxamide (a). 5-Cyano-4-(3-nitrophenyl)-2-phenyl-6-hydroxy-pyrimidine A mixture of benzamidine hydrochloride (16.4 g), 3-nitrobenzaldehyde (15.1 g), ethyl cyanoacetate (11.2 ml) and potassium carbonate (16.6 g) in abs. EtOH (250 ml) was stirred at 60° C. for 8 h. The reaction mixture was cooled to 0° C. in an ice bath. The resulting precipitate was filtered off, washed with abs. EtOH and heated in water (100° C.) until a clear solution was obtained. The solution was cooled to 50° C., acidified to pH 2 by adding 2N aq. HCl and cooled to 0° C. in an ice bath. The resulting precipitate was filtered off and washed with ice water. Residual water was removed by coevaporation with 1,4-dioxane.

Yield: 15.0 g. MS-ESI: [M+H]⁺=319.2 TLC: $R_f$=0.3, silica gel, DCM/MeOH=9/1 (v/v).

(b). 6-Chloro-5-cyano-4-(3-nitrophenyl)-2-phenyl-pyrimidine

POCl₃ (50 ml) was added to a stirred solution of 5-cyano-4-(3-nitrophenyl)-2-phenyl-6-hydroxy-pyrimidine (example 9(a), 15.0 g) and dimethylaniline (0.5 ml) in dry 1,4-dioxane p.a. (200 ml). After 3 h at 90° C., the warm mixture was filtered off and the filtrate was concentrated under reduced pressure. The residue was dissolved in 1,4-dioxane and ice water was added. The resulting precipitate was filtered off and washed with water. Residual water was removed by coevaporation with 1,4-dioxane.

Yield: 15.8 g MS-ESI: [M+H]⁺=337.4 TLC: $R_f$=0.8, silica gel, heptane/EtOAc=3/2 (v/v).

(c). Ethyl 5-cyano-4-(3-nitrophenyl)-2-phenyl-6-(ethoxycarbonylmethylthio)-pyrimidine DIPEA (8.71 ml) was added to a stirred solution of ethyl 2-mercaptoacetate (5.15 ml) and 6-chloro-5-cyano-4-(3-nitrophenyl)-2-phenyl-pyrimidine (example 9(b), 15.8 g) in a mixture of EtOH (125 ml) and DCM (125 ml) under a nitrogen atmosphere. After 2 h at room temperature, the mixture was diluted with DCM until complete dissolution, washed with 0.5N aq. HCl, dried (MgSO₄) and concentrated under reduced pressure.

Yield: 19.7 g MS-ESI: [M+H]⁺=421.2. TLC: Rf=0.7, silica gel, heptane/EtOAc=3/2 (v/v).

(d). Ethyl 5-amino-4-(3-nitrophenyl)-2-phenyl-thieno[2,3-d]pyrimidine-6-carboxylate DIPEA (20.0 ml) was added to a stirred solution of ethyl 5-cyano-4-(3-nitrophenyl)-2-phenyl-6-(ethoxycarbonylmethylthio)-pyrimidine (example 9(c), 19.7 g) in a mixture of abs. EtOH (100 ml) and toluene p.a. (100 ml). After 48 h at 100° C., the mixture was cooled to 0° C. The resulting precipitate was filtered off, washed with cold EtOH and dried in vacuo at 40° C.

Yield: 17.0 g MS-ESI: [M+H]⁺=421.2 TLC: $R_f$=0.5, silica gel, heptane/EtOAc=3/2 (v/v).

(e). Ethyl 5-amino-4-(3-aminophenyl)-2-phenyl-thieno[2,3-d]pyrimidine-6-carboxylate A solution of tin (II) chloride (23.0 g) in abs. EtOH (250 ml) was added to a solution of ethyl 5-amino-4-(3-nitrophenyl)-2-phenyl-thieno[2,3-d]pyrimidine-6-carboxylate (example 9(d), 16.6 g) in 1,4-dioxane p.a (250 ml). 37% aq. HCl (6.9 ml) was added and the mixture was heated under reflux (90° C.) for 16 h. The mixture was allowed to cool to room temperature and concentrated under reduced pressure. The residue was suspended in EtOAc (500 ml). 4N aq. NaOH was added to obtain a pH of 10-11. The mixture was diluted by adding sat. aq. NaCl. The organic layer was separated, dried (MgSO₄) and concentrated under reduced pressure.

Yield: 17.0 g MS-ESI: [M+H]⁺=421.2 TLC: $R_f$=0.5, silica gel, heptane/EtOAc=3/2 (v/v).

(f). 5-Amino-4-(3-aminophenyl)-2-phenyl-thieno[2,3-d]pyrimidine-6-carboxylic acid Potassium hydroxide (20.0 g) was added to a solution of ethyl 5-amino-4-(3-aminophenyl)-2-phenyl-thieno[2,3-d]pyrimidine-6-carboxylate (example 9(e), 17.0 g) in a mixture of 1,4-dioxane (210 ml) and water (80 ml). After 16 h at 90° C., the mixture was cooled to 0° C. The resulting precipitate was filtered off, suspended in water (300 ml) and cooled to 0° C. The mixture was acidified to pH 3 by adding 2N aq. citric acid and stirred at 0° C. up to room temperature for 2 h. The resulting precipitate was filtered off, washed with water and dried in vacuo at 40° C.

Yield: 13.3 g MS-ESI: $[M+H]^+$=363.0 TLC: $R_f$=0.2, silica gel, DCM/MeOH=95/5 (v/v).

(g). tert-Butyl 5-amino-4-(3-aminophenyl)-2-phenyl-thieno[2,3-d]pyrimidine-6-carboxamide DIPEA (15.3 ml), tert-butylamine (9.3 ml) and TBTU (14.1 g) were added to a mixture of 5-amino-4-(3-aminophenyl)-2-phenyl-thieno[2,3-d]pyrimidine-6-carboxylic acid (example 9(f), 13.3 g) in a mixture of DCM (250 ml) and DMF (50 ml) under a nitrogen atmosphere. After 3 h at room temperature, the mixture was diluted with DCM and washed with sat. aq. $NaHCO_3$, 0.1N aq. HCl and sat. aq. NaCl. The organic layer was dried ($MgSO_4$) and concentrated under reduced pressure. The crud product was purified by chromatography on silica gel, using heptane/EtOAc=3/7 to 1/1 (v/v) as eluent.

Yield: 14.7 g MS-ESI: $[M+H]^+$=418.4 TLC: $R_f$=0.4, silica gel, heptane/EtOAc=3/2 (v/v).

(h). tert-Butyl 5-amino-4-(3-(2-bromoacetamido)-phenyl)-2-phenyl-thieno[2,3-d]pyrimidine-6-carboxamide Bromoacetyl chloride (2.80 ml) was added dropwise to a solution of tert-butyl 5-amino-4-(3-aminophenyl)-2-phenyl-thieno[2,3-d]pyrimidine-6-carboxamide (example 9(g), 5.8 g) and DIPEA (12.2 ml) in DCM (50 ml). After 3 h at room temperature, the mixture was diluted with DCM, washed with sat. aq. $NaHCO_3$, dried ($MgSO_4$) and concentrated under reduced pressure. The crude product was purified by chromatography on silica gel using heptane/EtOAc=3/2 (v/v) as eluent. A 1:1 (mol/mol) mixture of tert-butyl 5-amino-4-(3-(2-bromoacetamido)-phenyl)-2-phenyl-thieno[2,3-d]pyrimidine-6-carboxamide and tert-butyl 5-amino-4-(3-(2-chloroacetamido)-phenyl)-2-phenyl-thieno[2,3-d]pyrimidine-6-carboxamide was obtained.

Yield: 2.6 g MS-ESI: $[M+H]^+$=540.2, $[M'+H]^+$=494.2 TLC: Rf=0.3, silica gel, heptane/EtOAc=3/2 (v/v).

(i). tert-Butyl 5-amino-2-phenyl-4-(3-((N-ethyl-N-(2-hydroxyethyl)-glycinyl)-amino)-phenyl)-thieno[2,3-d]pyrimidine-6-carboxamide To a stirred solution of tert-butyl 5-amino-4-(3-(2-bromoacetamido)-phenyl)-2-phenyl-thieno[2,3-d]pyrimidine-6-carboxamide (example 9(h), 500 mg) in DCM (5 ml) was added N-ethyl-2-amino-ethanol (500 mg). After stirring for 17 h at room temperature, the reaction mixture was diluted with DCM (100 ml), washed with aq. $NaHCO_3$ (1 M, 2×50 ml), dried ($MgSO_4$) and concentrated in vacuo. The residue was purified by HPLC using a Luna C-18 column with the following gradient: 0.1% aq. TFA+10% aq. ACN/ACN=90/10 to 10/90 (v/v) in 30 min. The title compound was then lyophilized from a mixture of 1,4-dioxane, 0.1% aq. TFA and water.

Yield: 271 mg (TFA-salt) MS-ESI: $[M+H]^+$=547.2 HPLC: $R_t$=11.88 min, column Luna C-18(2), 3 μm, 100×2.0 mm, detection UV=210 nm, oven temperature=40° C., flow=0.25 ml/min, eluent phosphate buffer 50 mM pH 2.1/water/ACN=10/80/10 to 10/10/80 (v/v/v), run time=20 min.

Example 10 tert-Butyl 5-amino-2-phenyl-4-(3-(N-(methoxycarbonylmethyl)-glycinyl)-amino)-phenyl)-thieno[2,3-d]pyrimidine-6-carboxamide To a stirred solution of tert-butyl 5-amino-4-(3-(2-bromoacetamido)-phenyl)-2-phenyl-thieno[2,3-d]pyrimidine-6-carboxamide (example 9(h), 500 mg) and N,N-diisopropylethyl amine (DiPEA, 1 ml) in DCM (5 ml) was added glycine methyl ester hydrochloride (700 mg). After stirring for 17 h at room temperature, the reaction mixture was diluted with DCM (100 ml), washed with aq. $NaHCO_3$ (1 M, 2×50 ml), dried ($MgSO_4$) and concentrated in vacuo. The residue was purified by HPLC using a Luna C-18 column with the following gradient: 0.1% aq. TFA+10% aq. ACN/ACN=90/10 to 10/90 (v/v) in 30 min. The title compound was then lyophilized from a mixture of 1,4-dioxane, 0.1% aq. TFA and water.

Yield: 321 mg (TFA-salt) MS-ESI: $[M+H]^+$=547.2 HPLC: $R_t$=12.54 min, column Luna C-18(2), 3 μm, 100×2.0 mm, detection UV=210 nm, oven temperature=40° C., flow=0.25 ml/min, eluent phosphate buffer 50 mM pH 2.1/water/ACN=10/80/10 to 10/10/80 (v/v/v), run time=20 min.

Example 11 tert-Butyl 5-amino-2-(2-furyl)-4-(3-((N-methyl-N-(2-hydroxyethyl)-glycinyl)-amino)-phenyl)-thieno[2,3-d]pyrimidine-6-carboxamide (a) 2-amidinofuran Cooled (0° C.) and saturated ethanolic HCl (40 ml) was added to a cooled (ice-bath, 0° C.) reaction vessel, containing 2-furonitril (13 ml). The resulting solution was allowed to reach ambient temperature and stirred under a nitrogen atmosphere for 48 h. After concentration of the reaction mixture in vacuo, the residue, containing the corresponding 2-furyl ethyl imidate, was redissolved in ethanol (20 ml) and stirred at 0° C. under a nitrogen atmosphere. Subsequently, saturated ethanolic ammonia (40 ml) was added and the reaction mixture was stirred in a sealed reaction vessel for 48 h. After filtration of the reaction mixture, the filtrate was concentrated under reduced pressure. The crude compound was used without further purification in the next step.

Yield: 15.0 g (b). 5-Cyano-4-(3-nitrophenyl)-2-(2-furyl)-6-hydroxy-pyrimidine

A mixture of 2-amidinofuran (example 11(a), 15 g), 3-nitrobenzaldehyde (24 g), ethyl cyanoacetate (17 ml) and potassium carbonate (25 g) in abs. EtOH (300 ml) was stirred at 60° C. for 16 h. The reaction mixture was cooled to 0° C. in an ice bath. The resulting precipitate was filtered off, washed with abs. EtOH and heated in water (100° C.) under stirring until a milky suspension was obtained. The suspension was cooled to 50° C., acidified to pH 2 by adding 2N aq. HCl and cooled to 0° C. in an ice bath. The resulting precipitate was filtered off and washed with ice water. Residual water was removed by coevaporation with 1,4-dioxane.

Yield: 16.0 g MS-ESI: [M+H]⁺=309.2 TLC: $R_f$=0.3, silica gel, DCM/MeOH=9/1 (v/v).

(c). 6-Chloro-5-cyano-4-(3-nitrophenyl)-2-(2-furyl)-pyrimidine

POCl₃ (50 ml) was added to a stirred solution of 5-cyano-4-(3-nitrophenyl)-2-(2-furyl)-6-hydroxy-pyrimidine (example 11(b), 16.0 g) and dimethylaniline (0.5 ml) in dry 1,4-dioxane p.a. (250 ml). After 2 h at 90° C., the warm mixture was filtered off and the filtrate was concentrated under reduced pressure. The residue was dissolved in 1,4-dioxane and ice water was added. The resulting precipitate was filtered off and washed with water. Residual water was removed by coevaporation with 1,4-dioxane.

Yield: 16.0 g MS-ESI: [M+H]⁺=327.2 TLC: $R_f$=0.75, silica gel, heptane/EtOAc=3/2 (v/v).

(d). Ethyl 5-Cyano-4-(3-nitrophenyl)-2-(2-furyl)-6-(ethoxycarbonylmethylthio)-pyrimidine DIPEA (9.1 ml) was added to a stirred solution of ethyl 2-mercaptoacetate (5.4 ml) and 6-chloro-5-cyano-4-(3-nitrophenyl)-2-(2-furyl)-pyrimidine (example 11(c), 16.0 g) in a mixture of EtOH (125 ml) and DCM (125 ml) under a nitrogen atmosphere. After 2 h at room temperature, the mixture was diluted with DCM until complete dissolution, washed with 0.5N aq. HCl, dried (MgSO₄) and concentrated under reduced pressure.

Yield: 20.0 g MS-ESI: [M+H]⁺=411.2. TLC: Rf=0.7, silica gel, heptane/EtOAc=3/2 (v/v).

(e). Ethyl 5-amino-4-(3-nitrophenyl)-2-(2-furyl)-thieno[2,3-d]pyrimidine-6-carboxylate DIPEA (20.0 ml) was added to a stirred solution of ethyl 5-cyano-4-(3-nitrophenyl)-2-(2-furyl)-6-(ethoxycarbonylmethylthio)-pyrimidine (example 11(d), 20 g) in a mixture of abs. EtOH (100 ml) and toluene p.a. (100 ml). After 48 h at 100° C., the mixture was cooled to 0° C. The resulting precipitate was filtered off, washed with cold EtOH and dried in vacuo at 40° C.

Yield: 20 g MS-ESI: [M+H]⁺=411.2 TLC: $R_f$=0.6, silica gel, heptane/EtOAc=3/2 (v/v).

(f). Ethyl 5-amino-4-(3-aminophenyl)-2-(2-furyl)-thieno[2,3-d]pyrimidine-6-carboxylate A solution of tin (II) chloride (28.0 g) in abs. EtOH (250 ml) was added to a solution of ethyl 5-amino-4-(3-nitrophenyl)-2-(2-furyl)-thieno[2,3-d]pyrimidine-6-carboxylate (example 11(e), 20 g) in 1,4-dioxane p.a. (250 ml). 37% aq. HCl (8.5 ml) was added and the mixture was heated under reflux (90° C.) for 16 h. The mixture was allowed to cool to room temperature and concentrated under reduced pressure. The residue was suspended in EtOAc (500 ml). 4N aq. NaOH was added to obtain a pH of 10-11. The mixture was diluted by adding sat. aq. NaCl. The organic layer was separated, dried (MgSO₄) and concentrated under reduced pressure.

Yield: 17.5 g MS-ESI: [M+H]⁺=381.2 TLC: $R_f$=0.4, silica gel, heptane/EtOAc=3/2 (v/v).

(g). 5-Amino-4-(3-aminophenyl)-2-(2-furyl)-thieno[2,3-d]pyrimidine-6-carboxylic acid Potassium hydroxide (23.0 g) was added to a solution of ethyl 5-amino-4-(3-aminophenyl)-2-(2-furyl)-thieno[2,3-d]pyrimidine-6-carboxylate (example 11(f), 17.5 g) in a mixture of 1,4-dioxane (210 ml) and water (80 ml). After 8 h at 90° C., the mixture was cooled to 0° C. The resulting precipitate was filtered off, suspended in water (300 ml) and cooled to 0° C. The mixture was acidified to pH 3 by adding 2N aq. citric acid and stirred at 0° C. up to room temperature for 2 h. The resulting precipitate was filtered off, washed with water and dried in vacuo at 40° C.

Yield: 16.9 g MS-ESI: [M+H]⁺=353.2 TLC: $R_f$=0.2, silica gel, DCM/MeOH=95/5 (v/v).

(h). tert-Butyl 5-amino-4-(3-aminophenyl)-2-(2-furyl)-thieno[2,3-d]pyrimidine-6-carboxamide DIPEA (19.2 ml), tert-butylamine (11.6 ml) and TBTU (17.7 g) were added to a solution of 5-amino-4-(3-aminophenyl)-2-(2-furyl)-thieno[2,3-d]pyrimidine-6-carboxylic acid (example 11(g), 16.9 g) in a mixture of DCM (250 ml) and DMF (50 ml) under a nitrogen atmosphere. After 3 h at room temperature, a substantial amount of yellow precipitate had been formed, which was filtered off. The residue was washed with diethyl ether and dried in vacuo at 40° C.

Yield: 18.0 g MS-ESI: [M+H]⁺=408.2 TLC: $R_f$=0.4, silica gel, heptane/EtOAc=3/2 (v/v).

(i). tert-Butyl 5-amino-4-(3-(2-bromoacetamido)-phenyl)-2-(2-furyl)-thieno[2,3-d]pyrimidine-6-carboxamide Bromoacetyl chloride (100 l) was added dropwise to a solution of tert-butyl 5-amino-4-(3-aminophenyl)-2-(2-furyl)-thieno[2,3-d]pyrimidine-6-carboxamide (example 11(h), 250 mg) and DIPEA (0.5 ml) in DCM (5 ml). After 3 h at room temperature, the mixture was diluted with DCM, washed with sat. aq. NaHCO₃, dried (MgSO₄) and concentrated under reduced pressure. The crude product was purified by chromatography on silica gel using heptane/EtOAc=3/2 (v/v) as eluent. A 1:1 (mol/mol) mixture of tert-butyl 5-amino-4-(3-(2-bromoacetamido)-phenyl)-2-(2-thienyl)-thieno[2,3-d]pyrimidine-6-carboxamide and tert-butyl 5-amino-4-(3-(2-chloroacetamido)-phenyl)-2-(2-thienyl)-thieno[2,3-d]pyrimidine-6-carboxamide was obtained.

Yield: 124 mg MS-ESI: [M+H]⁺=540.2, [M'+H]⁺=494.2 TLC: Rf=0.3, silica gel, heptane/EtOAc=3/2 (v/v).

(j). tert-Butyl 5-amino-2-(2-furyl)-4-(3-((N-methyl-N-(2-hydroxyethyl)-glycinyl)-amino)-phenyl)-thieno[2,3-d]pyrimidine-6-carboxamide To a stirred solution of tert-butyl 5-amino-4-(3-(2-bromoacetamido)-phenyl)-2-(2-furyl)-thieno[2,3-d]pyrimidine-6-carboxamide (example 11(i), 130 mg) in DCM (5 ml) was added N-methyl-2-amino-ethanol (200 mg). After stirring for 17 h at room temperature, the reaction mixture was diluted with DCM (50 ml), washed with aq. NaHCO₃ (1 M, 2×10 ml), dried (MgSO₄) and concentrated in vacuo. The residue was purified by HPLC using a Luna C-18 column with the following gradient: 0.1% aq. TFA+10% aq. ACN/ACN=90/10 to 10/90 (v/v) in 30 min. The title compound was then lyophilized from a mixture of 1,4-dioxane, 0.1% aq. TFA and water.

Yield: 81 mg (TFA-salt) MS-ESI: [M+H]⁺=523.2 HPLC: $R_t$=11.01 min, column Luna C-18(2), 3 µm, 100×2.0 mm, detection UV=210 nm, oven temperature=40° C., flow=0.25 ml/min, eluent phosphate buffer 50 mM pH 2.1/water/ACN=10/80/10 to 10/10/80 (v/v/v), run time=20 min.

Example 12 tert-Butyl 5-amino-2-(2-furyl)-4-(3-(N-(1-hydroxy-2-methyl-prop-2-yl)-glycinyl)-amino)-phen 2,3-d]pyrimidine-6-carboxamide To a stirred solution of tert-butyl 5-amino-4-(3-(2-bromoacetamido)-phenyl)-2-(2-furyl)-thieno[2,3-d]pyrimidine-6-carboxamide (example 11(i), 130 mg) in DCM (5 ml) was added 2-amino-2-methyl-propanol (260 mg). After stirring for 17 h at room temperature, the reaction mixture was diluted with DCM (50 ml), washed with aq. NaHCO$_3$ (1 M, 2×10 ml), dried (MgSO$_4$) and concentrated in vacuo. The residue was purified by HPLC using a Luna C-18 column with the following gradient: 0.1% aq. TFA+10% aq. ACN/ACN=90/10 to 10/90 (v/v) in 30 min. The title compound was then lyophilized from a mixture of 1,4-dioxane, 0.1% aq. TFA and water.

Yield: 54 mg (TFA-salt) MS-ESI: [M+H]$^+$=537.2 HPLC: R$_t$=11.15 min, column Luna C-18(2), 3 μm, 100×2.0 mm, detection UV=210 nm, oven temperature=40° C., flow=0.25 ml/min, eluent phosphate buffer 50 mM pH 2.1/water/ACN=10/80/10 to 10/10/80 (v/v/v), run time=20 min.

Example 13 tert-Butyl 5-amino-2-(2-furyl)-4-(3-(N-(methoxycarbonylmethyl)-glycinyl)-amino)-phenyl)-thieno[2,3-d]pyrimidine-6-carboxamide To a stirred solution of tert-butyl 5-amino-4-(3-(2-bromoacetamido)-phenyl)-2-(2-furyl)-thieno[2,3-d]pyrimidine-6-carboxamide (example 11(i), 130 mg) and DIPEA (0.5 ml) in DCM (5 ml) was added glycine methyl ester hydrochloride (324 mg). After stirring for 17 h at room temperature, the reaction mixture was diluted with DCM (50 ml), washed with aq. NaHCO$_3$ (1 M, 2×10 ml), dried (MgSO$_4$) and concentrated in vacuo. The residue was purified by HPLC using a Luna C-18 column with the following gradient: 0.1% aq. TFA+10% aq. ACN/ACN=90/10 to 10/90 (v/v) in 30 min. The title compound was then lyophilized from a mixture of 1,4-dioxane, 0.1% aq. TFA and water.

Yield: 74 mg (TFA-salt) MS-ESI: [M+H]$^+$=537.2 HPLC: R$_t$=12.09 min, column Luna C-18(2), 3 μm, 100×2.0 mm, detection UV=210 nm, oven temperature=40° C., flow=0.25 m/min, eluent phosphate buffer 50 mM pH 2.1/water/ACN=10/80/10 to 10/10/80 (v/v/v), run time=20 min.

Example 14 tert-Butyl 5-amino-2-(2-thienyl)-4-(3-((N-methyl-N-(2-hydroxyethyl)-glycinyl)-amino)-phenyl)-thieno[2,3-d]pyrimidine-6-carboxamide (a). 5-Cyano-4-(3-nitrophenyl)-2-(2-thienyl)-6-hydroxy-pyrimidine A mixture of 2-amidinothiophene hydrochloride (10.0 g), 3-nitrobenzaldehyde (9.7 g), ethyl cyanoacetate (6.81 ml) and potassium carbonate (10.1 g) in abs. EtOH (200 ml) was stirred at 60° C. for 8 h. The reaction mixture was cooled to 0° C. in an ice bath, filtered, washed with abs. EtOH and the residue was dissolved in water (100° C.). The solution was cooled to 50° C., acidified with 2N aq. HCl to pH 2 and cooled to 0° C. in an ice bath. The resulting precipitate was filtered off and washed with ice water. Residual water was removed by coevaporation with 1,4-dioxane.

Yield: 10.0 g MS-ESI: [M+H]$^+$=325.0 TLC: R$_f$=0.3, silica gel, DCM/MeOH=9/1 (v/v).

(b). 6-Chloro-5-cyano-4-(3-nitrophenyl)-2-(2-thienyl)-pyrimidine

POCl$_3$ (30 ml) was added to a stirred solution of 5-cyano-4-(3-nitrophenyl)-2-(2-thienyl)-6-hydroxy-pyrimidine (example 14(a), 10.0 g) and dimethylaniline (a few drops) in dry 1,4-dioxane (150 ml). After 3 h at 90° C., the mixture was cooled to room temperature and concentrated under reduced pressure. The residue was dissolved in 1,4-dioxane and ice water was cautiously added. The resulting precipitate was filtered off and washed with water. Residual water was removed by coevaporation with 1,4-dioxane and drying in vacuo at 40° C.

Yield: 9.8 g MS-ESI: [M+H]$^+$=343.4 TLC: R$_f$=0.8, silica gel, heptane/EtOAc=3/2 (v/v).

(c). Ethyl 5-cyano-4-(3-nitrophenyl)-2-(2-thienyl)-6-(ethoxycarbonylmethylthio)-pyrimidine DIPEA (5.57 ml) was added to a stirred solution of ethyl 2-mercaptoacetate (3.28 ml) and 6-chloro-5-cyano-4-(3-nitrophenyl)-2-(2-thienyl)-pyrimidine (example 14(b), 9.8 g) in a mixture of EtOH (80 ml) and DCM (80 ml) under a nitrogen atmosphere. After 2 h at room temperature, the mixture was diluted with DCM until complete dissolution, washed with 0.5N aq. HCl, dried (MgSO$_4$) and concentrated under reduced pressure.

Yield: 12.9 g MS-ESI: [M+H]$^+$=427.2 TLC: R$_f$=0.7, silica gel, heptane/EtOAc=3/2 (v/v).

(d). Ethyl 5-amino-4-(3-nitrophenyl)-2-(2-thienyl)-thieno[2,3-d]pyrimidine-6-carboxylate DIPEA (13.0 ml) was added to a stirred solution of ethyl 5-cyano-4-(3-nitrophenyl)-2-(2-thienyl)-6-(ethoxycarbonylmethylthio)-pyrimidine (example 14(c), 12.9 g) in a mixture of abs. EtOH (75 ml) and toluene p.a. (75 ml). After 48 h at 100° C., the mixture was cooled to 0° C. The resulting precipitate was filtered off, washed with cold EtOH and dried in vacuo at 40° C.

Yield: 11.0 g MS-ESI: [M+H]$^+$=427.2 TLC: R$_f$=0.6, silica gel, heptane/EtOAc=3/2 (v/v).

(e). Ethyl 5-amino-4-(3-aminophenyl)-2-(2-thienyl)-thieno[2,3-d]pyrimidine-6-carboxylate A solution of tin (II) chloride (15 g) in abs. EtOH (150 ml) was added to a solution of ethyl 5-amino-4-(3-nitrophenyl)-2-(2-thienyl)-thieno[2,3-d]pyrimidine-6-carboxylate (example 14(d), 10.86 g) in 1,4-dioxane (150 ml). 37% aq. HCl (4.5 ml) was added and the mixture was heated under reflux for 16 h. The mixture was allowed to cool to room temperature and concentrated under reduced pressure. The residue was suspended in EtOAc (400 ml) and THF was added until complete dissolution. 4N aq. NaOH was added to obtain a pH of 10-11. The mixture was diluted by adding sat. aq. NaCl. The organic layer was separated, dried (MgSO$_4$) and concentrated under reduced pressure.

Yield: 12.0 g MS-ESI: [M+H]$^+$=397.2 TLC: R$_f$=0.4, silica gel, heptane/EtOAc=3/2 (v/v).

(f). 5-Amino-4-(3-aminophenyl)-2-(2-thienyl)-thieno[2,3-d]pyrimidine-6-carboxylic acid Potassium hydroxide (13 g) was added to a solution of ethyl 5-amino-4-(3-aminophenyl)-2-(2-thienyl)-thieno[2,3-d]pyrimidine-6-carboxylate (example 14(e), 10.1 g) in a mixture of 1,4-dioxane (150 ml) and water (50 ml). After 16 h at 90° C., the mixture was cooled to 0° C. The resulting precipitate was filtered off, suspended in water (180 ml) and cooled to 0° C. The mixture was acidified to pH 3 by adding 2N aq. citric acid and stirred at 0° C. for 2 h. The resulting precipitate was filtered off, washed with water and dried in vacuo at 40° C.

Yield: 6.3 g MS-ESI: [M+H]$^+$=369.2 TLC: R$_f$=0.2, silica gel, DCM/MeOH=95/5 (v/v).

(g). tert-Butyl 5-amino-4-(3-aminophenyl)-2-(2-thienyl)-thieno[2,3-d]pyrimidine-6-carboxamide DIPEA (7.1 ml), tert-butylamine (4.3 ml) and TBTU (6.6 g) were added to a mixture of 5-amino-4-(3-aminophenyl)-2-(2-thienyl)-thieno[2,3-d]pyrimidine-6-carboxylic acid (example 14(f), 6.3 g) in a mixture of DCM (125 ml) and DMF (N,N-dimethylformamide) (25 ml) under a nitrogen atmosphere. After 3 h at room temperature, the mixture was diluted with DCM and washed with sat. aq. NaHCO$_3$, 0.1 N aq. HCl and sat. aq. NaCl. The organic layer was dried (MgSO$_4$) and concentrated under reduced pressure. The crude product was purified by chromatography on silica gel, using heptane/EtOAc=3/7 to 1/1 (v/v) as eluent.

Yield: 6.45 g MS-ESI: [M+H]$^+$=424.2 TLC: R$_f$=0.3, silica gel, heptane/EtOAc=3/2 (v/v).

(h). tert-Butyl 5-amino-4-(3-(2-bromoacetamido)-phenyl)-2-(2-thienyl)-thieno[2,3-d]pyrimidine-6-carboxamide Bromoacetyl chloride (2.40 ml) was added to a solution of tert-butyl 5-amino-4-(3-aminophenyl)-2-(2-thienyl)-thieno[2,3-d]pyrimidine-6-carboxamide (example 14(g), 5.0 g) and DIPEA (10.5 ml) in DCM (50 ml). After 3 h at room temperature, the mixture was diluted with DCM, washed with sat. aq. NaHCO$_3$, dried (MgSO$_4$) and concentrated under reduced pressure. The crude product was purified by chromatography on silica gel using heptane/EtOAc=3/2 (v/v) as eluent. A mixture of tert-butyl 5-amino-4-(3-(2-bromoacetamido)-phenyl)-2-(2-thienyl)-thieno[2,3-d]pyrimidine-6-carboxamide and tert-butyl 5-amino-4-(3-(2-chloroacetamido)-phenyl)-2-(2-thienyl)-thieno[2,3-d]pyrimidine-6-carboxamide was obtained.

Yield: 3.0 g MS-ESI: [M+H]$^+$=546.2, [M'+H]$^+$=500.2 TLC: R$_f$=0.2, silica gel, toluene/EtOAc=7/1 (v/v).

(i). tert-Butyl 5-amino-2-(2-thienyl)-4-(3-((N-methyl-N-(2-hydroxyethyl)-glycinyl)-amino)-phenyl)-thien 2,3-d]pyrimidine-6-carboxamide To a stirred solution of tert-butyl 5-amino-4-(3-(2-bromoacetamido)-phenyl)-2-(2-thienyl)-thieno[2,3-d]pyrimidine-6-carboxamide (example 14(h), 100 mg) in DCM (5 ml) was added N-methyl-2-aminoethanol (140 mg). After stirring for 17 h at room temperature, the reaction mixture was diluted with DCM (50 ml), washed with aq. NaHCO$_3$ (1 M, 2×10 ml), dried (MgSO$_4$) and concentrated in vacuo. The residue was purified by HPLC using a Luna C-18 column with the following gradient: 0.1% aq. TFA+10% aq. ACN/ACN=90/10 to 10/90 (v/v) in 30 min. The title compound was then lyophilized from a mixture of 1,4-dioxane, 0.1% aq. TFA and water.

Yield: 59 mg (TFA-salt) MS-ESI: [M+H]$^+$=539.2 HPLC: R$_t$=11.01 min, column Luna C-18(2), 3 μm, 100×2.0 mm, detection UV=210 nm, oven temperature=40° C., flow=0.25 ml/min, eluent phosphate buffer 50 mM pH 2.1/water/ACN=10/80/10 to 10/10/80 (v/v/v), run time=20 min.

Example 15 tert-Butyl 5-amino-2-(2-thienyl)-4-(3-((N-(methoxycarbonylmethyl)-glycinyl)-amino)-phenyl)-thieno[2,3-d]pyrimidine-6-carboxamide To a stirred solution of tert-butyl 5-amino-4-(3-(2-bromoacetamido)-phenyl)-2-(2-thienyl)-thieno[2,3-d]pyrimidine-6-carboxamide (example 14(h), 100 mg) and DiPEA (0.5 ml) in DCM (5 ml) was added glycine methyl ester hydrochloride (250 mg). After stirring for 17 h at room temperature, the reaction mixture was diluted with DCM (50 ml), washed with aq. NaHCO$_3$ (1 M, 2×10 ml), dried (MgSO$_4$) and concentrated in vacuo. The residue was purified by HPLC using a Luna C-18 column with the following gradient: 0.1% aq. TFA+10% aq. ACN/ACN=90/10 to 10/90 (v/v) in 30 min. The title compound was then lyophilized from a mixture of 1,4-dioxane, 0.1% aq. TFA and water.

Yield: 74 mg (TFA-salt) MS-ESI: [M+H]$^+$=553.0 HPLC: R$_t$=12.57 min, column Luna C-18(2), 3 μm, 100×2.0 mm, detection UV=210 nm, oven temperature=40° C., flow=0.25 ml/min, eluent phosphate buffer 50 mM pH 2.1/water/ACN=10/80/10 to 10/10/80 (v/v/v), run time=20 min.

Example 16 tert-Butyl 5-amino-2-(2-thienyl)-4-(3-((N,N-di-(2-methoxyethyl)-glycinyl)-amino)-phenyl)-thieno[2,3-d]pyrimidine-6-carboxamide To a stirred solution of tert-butyl 5-amino-4-(3-(2-bromoacetamido)-phenyl)-2-(2-thienyl)-thieno[2,3-d]pyrimidine-6-carboxamide (example 14(h), 100 mg) in DCM (5 ml) was added N,N-di-(2-methoxyethyl)-amine (200 mg). After stirring for 17 h at room temperature, the reaction mixture was diluted with DCM (50 ml), washed with aq. NaHCO$_3$ (1 M, 2×10 ml), dried (MgSO$_4$) and concentrated in vacuo. The residue was purified by HPLC using a Luna C-18 column with the following gradient: 0.1% aq. TFA+10% aq. ACN/ACN=90/10 to 10/90 (v/v) in 30 min. The title compound was then lyophilized from a mixture of 1,4-dioxane, 0.1% aq. TFA and water.

Yield: 59 mg (TFA-salt) MS-ESI: [M+H]$^+$=597.4 HPLC: R$_t$=13.84 min, column Luna C-18(2), 3 μm, 100×2.0 mm, detection UV=210 nm, oven temperature=40° C., flow=0.25 ml/min, eluent phosphate buffer 50 mM pH 2.1/water/ACN=10/80/10 to 10/10/80 (v/v/v), run time=20 min.

Example 17 tert-Butyl 5-amino-2-ethylamino-4-(3-((N-ethyl-N-(2-methoxyethyl)-glycinyl)-amino)-phenyl)-thieno[2,3-d]pyrimidine-6-carboxamide (a). tert-Butyl 5-amino-2-methanesulfinyl-4-(3-((N-ethyl-N-(2-methoxyethyl)-glycinyl)-amino)-phenyl)-thieno[2,3-d]pyrimidine-6-carboxamide To a stirred solution of tert-butyl 5-amino-2-methylthio-4-(3-((N-ethyl-N-(2-methoxyethyl)-glycinyl)-amino)-phenyl)-thieno[2,3-d]pyrimidine-6-carboxamide (example 4, 1.0 g) in trifluoroacetic acid (TFA, 25 ml) was added 3-chloroperbenzoic acid (m-CPBA, 1.0 g). After 17 h, the reaction mixture was concentrated under reduced pressure at ambient temperature (20° C.), redissolved in DCM (100 ml), carefully washed with sat. aq. NaHCO$_3$ (2×50 ml) and water (50 ml), dried (MgSO$_4$) and concentrated in vacuo. The crude residue was used without further purification in the next step.

Yield: 820 mg MS-ESI: [M+H]$^+$=547.3 TLC: R$_f$=0.2, silica gel, DCM/MeOH=9/1 (v/v).

(b). tert-Butyl 5-amino-2-ethylamino-4-(3-((N-ethyl-N-(2-methoxyethyl)-glycinyl)-amino)-phenyl)-thieno[2,3-d]pyrimidine-6-carboxamide Ethyl amine hydrochloride (150 mg) was added to a stirred solution of tert-butyl 5-amino-2-methanesulfinyl-4-(3-((N-ethyl-N-(2-methoxyethyl)-glycinyl)-amino)-phenyl)-thieno[2,3-d]pyrimidine-6-carboxamide (example 17(a), 100 mg) and DiPEA (0.5 ml) in 1,4-dioxane (5 ml) and the reaction mixture was heated to 60° C. for 3 h. After concentration of the reaction mixture under reduced pressure, the residue was taken up in DCM (50 ml) and washed with brine (1 M, 25 ml) and water (25 ml). Subsequently, the organic layer was dried (MgSO$_4$) and concentrated in vacuo. The thus obtained residue was purified by HPLC using a Luna C-18 column with the following gradient: 0.1% aq. TFA+10% aq. ACN/ACN=90/10 to 10/90 (v/v) in 30 min. The title compound was then lyophilized from a mixture of 1,4-dioxane, 0.1% aq. TFA and water.

Yield: 36 mg (TFA-salt) MS-ESI: [M+H]$^+$=528.4 HPLC: R$_t$=10.21 min, column Luna C-18(2), 3 μm, 100×2.0 mm, detection UV=210 nm, oven temperature=40° C., flow=0.25 ml/min, eluent phosphate buffer 50 mM pH 2.1/water/ACN=10/80/10 to 10/10/80 (v/v/v), run time=20 min.

Example 18 tert-Butyl 5-amino-2-(N,N-dimethylamino)-4-(3-((N-methyl-N-(2-hydroxyethyl)-glycinyl)-amino)-phenyl)-thieno[2,3-d]pyrimidine-6-carboxamide (a). tert-Butyl 5-amino-2-methanesulfinyl-4-(3-((N-methyl-N-(2-hydroxyethyl)-glycinyl)-amino)-phenyl)-thieno[2,3-d]pyrimidine-6-carboxamide To a stirred solution of tert-butyl 5-amino-2-methylthio-4-(3-((N-methyl-N-(2-hydroxyethyl)-glycinyl)-amino)-phenyl)-thieno[2,3-d]pyrimidine-6-carboxamide (example 1(i), 1.0 g) in trifluoroacetic acid (TFA, 25 ml) was added 3-chloroperbenzoic acid (m-CPBA, 1.0 g). After 17 h, the reaction mixture was concentrated under reduced pressure at ambient temperature (20° C.), redissolved in DCM (100 ml), carefully washed with sat. aq. NaHCO$_3$ (2×50 ml) and water (50 ml), dried (MgSO$_4$) and concentrated in vacuo. The crude residue was used without further purification in the next step.

Yield: 910 mg MS-ESI: [M+H]$^+$=519.6 TLC: R$_f$=0.15, silica gel, DCM/MeOH=9/1 (v/v).

(b). tert-Butyl 5-amino-2-(N,N-dimethylamino)-4-(3-((N-methyl-N-(2-hydroxyethyl)-glycinyl)-amino)-phenyl)-thi 2,3-d]pyrimidine-6-carboxamide Dimethyl amine hydrochloride (150 mg) was added to a stirred solution of tert-butyl 5-amino-2-methanesulfinyl-4-(3-((N-methyl-N-(2-hydroxyethyl)-glycinyl)-amino)-phenyl)-thieno[2,3-d]pyrimidine-6-carboxamide (example 18(a), 100 mg) and DiPEA (0.5 ml) in 1,4-dioxane (5 ml) and the reaction mixture was heated to 60° C. for 3 h. After concentration of the reaction mixture under reduced pressure, the residue was taken up in DCM (50 ml) and washed with brine (1 M, 25 ml) and water (25 ml). Subsequently, the organic layer was dried (MgSO$_4$) and concentrated in vacuo. The thus obtained residue was purified by HPLC using a Luna C-18 column with the following gradient: 0.1% aq. TFA+10% aq. ACN/ACN=90/10 to 10/90 (v/v) in 30 min. The title compound was then lyophilized from a mixture of 1,4-dioxane, 0.1% aq. TFA and water.

Yield: 36 mg (TFA-salt) MS-ESI: [M+H]$^+$=500.2 HPLC: R$_t$=10.03 min, column Luna C-18(2), 3 μm, 100×2.0 mm, detection UV=210 nm, oven temperature=40° C., flow=0.25 ml/min, eluent phosphate buffer 50 mM pH 2.1/water/ACN=10/80/10 to 10/10/80 (v/v/v), run time=20 min.

Example 19 tert-Butyl 5-amino-2-ethylamino-4-(3-((N-(methoxycarbonylmethyl)-glycinyl)-amino)-phenyl)-thieno[2,3-d]pyrimidine-6-carboxamide (a). tert-Butyl 5-amino-2-methanesulfinyl-4-(3-((N-(methoxycarbonylmethyl)-glycinyl)-amino)-phenyl)-thieno[2,3-d]pyrimidine-6-carboxamide To a stirred solution of tert-butyl 5-amino-2-methylthio-4-(3-((N-(methoxycarbonylmethyl)-glycinyl)-amino)-phenyl)-t 2,3-d]pyrimidine-6-carboxamide (example 3, 1.0 g) in trifluoroacetic acid (TFA, 25 ml) was added 3-chloroperbenzoic acid (m-CPBA, 1.0 g). After 17 h, the reaction mixture was concentrated under reduced pressure at ambient temperature (20° C.), redissolved in DCM (100 ml), carefully washed with sat. aq. NaHCO$_3$ (2×50 ml) and water (50 ml), dried (MgSO$_4$) and concentrated in vacuo. The crude residue was used without further purification in the next step.

Yield: 680 mg MS-ESI: [M+H]$^+$=533.6 TLC: R$_f$=0.17, silica gel, DCM/MeOH=9/1 (v/v).

(b). tert-Butyl 5-amino-2-ethylamino-4-(3-((N-(methoxycarbonylmethyl)-glycinyl)-amino)-phenyl)-thieno[2,3-d]pyrimidine-6-carboxamide Ethyl amine hydrochloride (150 mg) was added to a stirred solution of tert-butyl 5-amino-2-methanesulfinyl-4-(3-((N-(methoxycarbonylmethyl)-glycinyl)-amino)-phenyl)-thieno[2,3-d]pyrimidine-6-carboxamide (example 19(a), 100 mg) and DiPEA (0.5 ml) in 1,4-dioxane (5 ml) and the reaction mixture was heated to 60° C. for 3 h. After concentration of the reaction mixture under reduced pressure, the residue was taken up in DCM (50 ml) and washed with brine (1 M, 25 ml) and water (25 ml). Subsequently, the organic layer was dried (MgSO$_4$) and concentrated in vacuo. The thus obtained residue was purified by HPLC using a Luna C-18 column with the following gradient: 0.1% aq. TFA+10% aq. ACN/ACN=90/10 to 10/90 (v/v) in 30 min. The title compound was then lyophilized from a mixture of 1,4-dioxane, 0.1% aq. TFA and water.

Yield: 57 mg (TFA-salt) MS-ESI: [M+H]$^+$=514.2 HPLC: R$_t$=12.56 min, column Luna C-18(2), 3 μm, 100×2.0 mm, detection UV=210 nm, oven temperature=40° C., flow=0.25 ml/min, eluent phosphate buffer 50 mM pH 2.1/water/ACN=10/80/10 to 10/10/80 (v/v/v), run time=20 min.

Example 20 tert-Butyl 5-amino-2-isopropylamino-4-(3-((N-ethyl-N-(2-methoxyethyl)-glycinyl)-amino)-phenyl)-thieno[2,3-d]pyrimidine-6-carboxamide Isopropyl amine (150 mg) was added to a stirred solution of tert-butyl 5-amino-2-methanesulfinyl-4-(3-((N-ethyl-N-(2-methoxyethyl)-glycinyl)-amino)-phenyl)-thieno[2,3-d]pyrimidine-6-carboxamide (example 17(a), 100 mg) and DiPEA (0.5 ml) in 1,4-dioxane (5 ml) and the reaction mixture was heated to 60° C. for 3 h. After concentration of the reaction mixture under reduced pressure, the residue was taken up in DCM (50 ml) and washed with brine (1 M, 25 ml) and water (25 ml). Subsequently, the organic layer was dried (MgSO$_4$) and concentrated in vacuo. The thus obtained residue was purified by HPLC using a Luna C-18 column with the following gradient: 0.1% aq. TFA+10% aq. ACN/ACN=90/10 to 10/90 (v/v) in 30 min. The title compound was then lyophilized from a mixture of 1,4-dioxane, 0.1% aq. TFA and water.

Yield: 57 mg (TFA-salt) MS-ESI: [M+H]$^+$=542.4 HPLC: R$_t$=11.01 min, column Luna C-18(2), 3 μm, 100×2.0 mm, detection UV=210 nm, oven temperature=40° C., flow=0.25 ml/min, eluent phosphate buffer 50 mM pH 2.1/water/ACN=10/80/10 to 10/10/80 (v/v/v), run time=20 min.

Example 21 tert-Butyl 5-amino-2-allylamino-4-(3-((N-(methoxycarbonylmethyl)-glycinyl)-amino)-phenyl)-thieno[2,3-d]pyrimidine-6-carboxamide Allyl amine (200 mg) was added to a stirred solution of tert-butyl 5-amino-2-methanesulfinyl-4-(3-((N-(methoxycarbonylmethyl)-glycinyl)-amino)-phenyl)-thieno[2,3-d]pyrimidine-6-carboxamide (example 19(a), 100 mg) and DiPEA (0.5 ml) in 1,4-dioxane (5 ml) and the reaction mixture was heated to 60° C. for 3 h. After concentration of the reaction mixture under reduced pressure, the residue was taken up in DCM (50 ml) and washed with brine (1 M, 25 ml) and water (25 ml). Subsequently, the organic layer was dried (MgSO$_4$) and concentrated in vacuo. The thus obtained is residue was purified by HPLC using a Luna C-18 column with the following gradient: 0.1% aq. TFA+10% aq. ACN/ACN=90/10 to 10/90 (v/v) in 30 min. The title compound was then lyophilized from a mixture of 1,4-dioxane, 0.1% aq. TFA and water.

Yield: 65 mg (TFA-salt) MS-ESI: [M+H]$^+$=526.4 HPLC: R$_t$=13.18 min, column Luna C-18(2), 3 μm, 100×2.0 mm, detection UV=210 nm, oven temperature=40° C., flow=0.25 ml/min, eluent phosphate buffer 50 mM pH 2.1/water/ACN=10/80/10 to 10/10/80 (v/v/v), run time=20 min.

Example 22 tert-Butyl 5-amino-2-methoxy-4-(3-((N-ethyl-N-(2-methoxyethyl)-glycinyl)-amino)-phenyl)-thieno[2,3-d]pyrimidine-6-carboxamide Potassium tert-butoxide (100 mg) was added to a stirred solution of tert-butyl 5-amino-2-methanesulfinyl-4-(3-((N-ethyl-N-(2-methoxyethyl)-glycinyl)-amino)-phenyl)-thieno[2,3-d]pyrimidine-6-carboxamide (example 17(a), 200 mg) in methanol (5 ml) and the reaction mixture was heated to 50° C. for 3 h. After concentration of the reaction mixture under reduced pressure, the residue was taken up in DCM (50 ml) and washed with aq. ammonium chloride (1 M, 25 ml), brine (1 M, 25 ml) and water (25 ml). Subsequently, the organic layer was dried (MgSO$_4$) and concentrated in vacuo. The thus obtained residue was purified by HPLC using a Luna C-18 column with the following gradient: 0.1% aq. TFA+10% aq. ACN/ACN=90/10 to 10/90 (v/v) in 30 min. The title compound was then lyophilized from a mixture of 1,4-dioxane, 0.1% aq. TFA and water.

Yield: 92 mg (TFA-salt) MS-ESI: [M+H]$^+$=515.4 HPLC: R$_t$=12.21 min, column Luna C-18(2), 3 μm, 100×2.0 mm, detection UV=210 nm, oven temperature=40° C., flow=0.25 ml/min, eluent phosphate buffer 50 mM pH 2.1/water/ACN=10/80/10 to 10/10/80 (v/v/v), run time=20 min.

Example 23 tert-Butyl 5-amino-2-allyloxy-4-(3-((N-ethyl-N-(2-methoxyethyl)-glycinyl)-amino)-phenyl)-thieno[2,3-d]pyrimidine-6-carboxamide Potassium tert-butoxide (100 mg) was added to a stirred solution of tert-butyl 5-amino-2-methanesulfinyl-4-(3-((N-ethyl-N-(2-methoxyethyl)-glycinyl)-amino)-phenyl)-thieno[2,3-d]pyrimidine-6-carboxamide (example 17(a), 200 mg) in allyl alcohol (5 ml) and the reaction mixture was heated to 50° C. for 3 h. After concentration of the reaction mixture under reduced pressure, the residue was taken up in DCM (50 ml) and washed with aq. ammonium chloride (1 M, 25 ml), brine (1 M, 25 ml) and water (25 ml). Subsequently, the organic layer was dried (MgSO$_4$) and concentrated in vacuo. The thus obtained residue was purified by HPLC using a Luna C-18 column with the following gradient: 0.1% aq. TFA+10% aq. ACN/ACN=90/10 to 10/90 (v/v) in 30 min. The title compound was then lyophilized from a mixture of 1,4-dioxane, 0.1% aq. TFA and water.

Yield: 63 mg (TFA-salt) MS-ESI: [M+H]$^+$=541.4 HPLC: R$_t$=12.71 min, column Luna C-18(2), 3 μm, 100×2.0 mm, detection UV=210 nm, oven temperature=40° C., flow=0.25 ml/min, eluent phosphate buffer 50 mM pH 2.1/water/ACN=10/80/10 to 10/10/80 (v/v/v), run time=20 min.

Example 24 tert-Butyl 5-amino-2-isopropoxy-4-(3-((N-ethyl-N-(2-methoxyethyl)-glycinyl)-amino)-phenyl)-thieno[2,3-d]pyrimidine-6-carboxamide Potassium tert-butoxide (100 mg) was added to a stirred solution of tert-butyl 5-amino-2-methanesulfinyl-4-(3-((N-ethyl-N-(2-methoxyethyl)-glycinyl)-amino)-phenyl)-thieno[2,3-d]pyrimidine-6-carboxamide (example 17(a), 200 mg) in isopropanol (5 ml) and the reaction mixture was heated to 50° C. for 3 h. After concentration of the reaction mixture under reduced pressure, the residue was taken up in DCM (50 ml) and washed with aq. ammonium chloride (1 M, 25 ml), brine (1 M, 25 ml) and water (25 ml). Subsequently, the organic layer was dried (MgSO$_4$) and concentrated in vacuo. The thus obtained residue was purified by HPLC using a Luna C-18 column with the following gradient: 0.1% aq. TFA+10% aq. ACN/ACN=90/10 to 10/90 (v/v) in 30 min. The title compound was then lyophilized from a mixture of 1,4-dioxane, 0.1% aq. TFA and water.

Yield: 32 mg (TFA-salt) MS-ESI: [M+H]$^+$=543.4 HPLC: R$_t$=12.93 min, column Luna C-18(2), 3 μm, 100×2.0 mm, detection UV=210 nm, oven temperature=40° C., flow=0.25 ml/min, eluent phosphate buffer 50 mM pH 2.1/water/ACN=10/80/10 to 10/10/80 (v/v/v), run time=20 min.

Example 25 tert-Butyl 5-amino-2-(4-pyridyl)-4-(3-((N-(1-hydroxy-2-methyl-prop-2-yl) -glycinyl)-amino)-phenyl)-thieno[2,3-d]pyrimidine-6-carboxamide (a). 5-Cyano-4-(3-nitrophenyl)-2-(4-pyridyl)-6-hydroxy-pyrimidine A mixture of 4-amidino-pyridine hydrochloride (16.5 g), 3-nitrobenzaldehyde (15.1 g), ethyl cyanoacetate (11.2 ml) and potassium carbonate (16.6 g) in abs. EtOH (250 ml) was stirred at 60° C. for 16 h. The reaction mixture was cooled to 0° C. in an ice bath. The resulting precipitate was filtered off, washed with abs. EtOH and heated in water (100° C.) until a clear solution was obtained. The solution was cooled to 50° C., acidified to pH 2 by adding 2N aq. HCl and cooled to 0° C. in an ice bath. The resulting precipitate was filtered off and washed with ice water. Residual water was removed by coevaporation with 1,4-dioxane.

Yield: 18.3 g MS-ESI: [M+H]$^+$=320.2 TLC: R$_f$=0.2, silica gel, DCM/MeOH=9/1 (v/v)

(b). 6-Chloro-5-cyano-4-(3-nitrophenyl)-2-(4-pyridyl)-pyrimidine

POCl$_3$ (50 ml) was added to a stirred solution of 5-cyano-4-(3-nitrophenyl)-2-(4-pyridyl)-6-hydroxy-pyrimidine (example 25(a), 18.3 g) and dimethylaniline (0.5 ml) in dry 1,4-dioxane p.a. (200 ml). After 3 h at 90° C., the warm mixture was filtered off and the filtrate was concentrated under reduced pressure. The residue was dissolved in 1,4-dioxane and ice water was added. The resulting precipitate was filtered off and washed with water. Residual water was removed by coevaporation with 1,4-dioxane.

Yield: 17.2 g MS-ESI: [M+H]$^+$=338.4 TLC: R$_f$=0.7, silica gel, heptane/EtOAc=3/2 (v/v)

(c). Ethyl 5-cyano-4-(3-nitrophenyl)-2-(4-pyridyl)-6-(ethoxycarbonylmethylthio)-pyrimidine DIPEA (9.8 ml) was added to a stirred solution of ethyl 2-mercaptoacetate (5.7 ml) and 6-chloro-5-cyano-4-(3-nitrophenyl)-2-(4-pyridyl)-pyrimidine (example 25(b), 17.2 g) in a mixture of EtOH (125 ml) and DCM (125 ml) under a nitrogen atmosphere. After 2 h at room temperature, the mixture was diluted with DCM until complete dissolution, washed with 0.5N aq. HCl, dried (MgSO$_4$) and concentrated under reduced pressure.

Yield: 20.5 g MS-ESI: [M+H]$^+$=422.0 TLC: Rf=0.6, silica gel, heptane/EtOAc=3/2 (v/v)

(d). Ethyl 5-amino-4-(3-nitrophenyl)-2-(4-pyridyl)-thieno[2,3-d]pyrimidine-6-carboxylate DIPEA (20.0 ml) was added to a stirred solution of ethyl 5-cyano-4-(3-nitrophenyl)-2-(4-pyridyl)-6-(ethoxycarbonylmethylthio)-pyrimidine (example 25(c), 20.5 g) in a mixture of abs. EtOH (100 ml) and toluene p.a. (100 ml). After 48 h at 100° C., the mixture was cooled to 0° C. The resulting precipitate was filtered off, washed with cold EtOH and dried in vacuo at 40° C.

Yield: 15.7 g MS-ESI: [M+H]$^+$=422.2 TLC: $R_f$=0.5, silica gel, heptane/EtOAc=3/2 (v/v).

(e). Ethyl 5-amino-4-(3-aminophenyl)-2-(4-pyridyl)-thieno[2,3-d]pyrimidine-6-carboxylate A solution of tin (II) chloride (21.0 g) in abs. EtOH (250 ml) was added to a solution of ethyl 5-amino-4-(3-nitrophenyl)-2-(4-pyridyl)-thieno[2,3-d]pyrimidine-6-carboxylate (example 25(d), 15.7 g) in 1,4-dioxane p.a. (250 ml). 37% aq. HCl (6.9 ml) was added and the mixture was heated under reflux (90° C.) for 16 h. The mixture was allowed to cool to room temperature and concentrated under reduced pressure. The residue was suspended in EtOAc (500 ml). 4N aq. NaOH was added to obtain a pH of 10-11. The mixture was diluted by adding sat. aq. NaCl. The organic layer was separated, dried (MgSO$_4$) and concentrated under reduced pressure.

Yield: 12.0 g MS-ESI: [M+H]$^+$=392.2 TLC: $R_f$=0.3, silica gel, heptane/EtOAc=3/2 (v/v).

(f). 5-Amino-4-(3-aminophenyl)-2-(4-pyridyl)-thieno[2,3-d]pyrimidine-6-carboxylic acid Potassium hydroxide (15.7 g) was added to a solution of ethyl 5-amino-4-(3-aminophenyl)-2-(4-pyridyl)-thieno[2,3-d]pyrimidine-6-carboxylate (example 25(e), 12.0 g) in a mixture of 1,4-dioxane (210 ml) and water (80 ml). After 16 h at 90° C., the mixture was cooled to 0° C. The resulting precipitate was filtered off, suspended in water (300 ml) and cooled to 0° C. The mixture was acidified to pH 3 by adding 2N aq. citric acid and stirred at 0° C. up to room temperature for 2 h. The resulting precipitate was filtered off, washed with water and dried in vacuo at 40° C.

Yield: 12.0 g MS-ESI: [M+H]$^+$=364.2 TLC: $R_f$=0.1, silica gel, DCM/MeOH=95/5 (v/v).

(g). tert-Butyl 5-amino-4-(3-aminophenyl)-2-(4-pyridyl)-thieno[2,3-d]pyrimidine-6-carboxamide DIPEA (12.9 ml), tert-butylamine (7.8 ml) and TBTU (11.9 g) were added to a mixture of 5-amino-4-(3-aminophenyl)-2-(4-pyridyl)-thieno[2,3-d]pyrimidine-6-carboxylic acid (example 25(f), 12.0 g) in a mixture of DCM (250 ml) and DMF (50 ml) under a nitrogen atmosphere. After 2 h at room temperature, the mixture was diluted with DCM and washed with sat. aq. NaHCO$_3$, 0.1N aq. HCl and sat. aq. NaCl. The organic layer was dried (MgSO$_4$) and concentrated under reduced pressure. The crude product was purified by chromatography on silica gel, using dichloromethane/methanol=1/0 to 95/5 (v/v) as eluent.

Yield: 12.2 g MS-ESI: [M+H]$^+$=419.4 TLC: $R_f$=0.3, silica gel, heptane/EtOAc=3/2 (v/v).

(h). tert-Butyl 5-amino-4-(3-(2-bromoacetamido)-phenyl)-2-(4-pyridyl)-thieno[2,3-d]pyrimidine-6-carboxamide A solution of bromoacetyl bromide (0.59 ml) in THF (25 ml) was added dropwise to a solution of tert-butyl 5-amino-4-(3-aminophenyl)-2-(4-pyridyl)-thieno[2,3-d]pyrimidine-6-carboxamide (example 25(g), 2.0 g) and N,N-dimethyl aniline (3.0 ml) in THF (50 ml). After 30 min at room temperature, the mixture was concentrated under reduced pressure, subsequently dissolved in DCM (100 ml), washed with sat. aq. NaHCO$_3$, dried (MgSO$_4$) and concentrated in vacuo. The residue was used without further purification in the next step.

Yield: 2.3 g MS-ESI: [M+H]$^+$=539.2 TLC: Rf=0.3, silica gel, heptane/EtOAc=3/2 (v/v).

(i). tert-Butyl 5-amino-2-(4-pyridyl)-4-(3-((N-(1-hydroxy-2-methyl-prop-2-yl) -glycinyl)-amino)-phenyl)-thieno[2,3-d]pyrimidine-6-carboxamide To a stirred solution of tert-butyl 5-amino-4-(3-(2-bromoacetamido)-phenyl)-2-(4-pyridyl)-thieno[2,3-d]pyrimidine-6-carboxamide (example 25(h), 200 mg) in DCM (5 ml) was added 2-amino-2-methyl-propanol (300 mg). After stirring for 17 h at room temperature, the reaction mixture was diluted with DCM (100 ml), washed with aq. NaHCO$_3$ (1 M, 2×50 ml), dried (MgSO$_4$) and concentrated in vacuo. The residue was purified by HPLC using a Luna C-18 column with the following gradient: 0.1% aq. TFA+10% aq. ACN/ACN=90/10 to 10/90 (v/v) in 30 min. The title compound was then lyophilized from a mixture of 1,4-dioxane, 0.1% aq. TFA and water.

Yield: 73 mg (TFA-salt) MS-ESI: [M+H]$^+$=548.2 HPLC: $R_t$=9.65 min, column Luna C-18(2), 3 μm, 100×2.0 mm, detection UV=210 nm, oven temperature=40° C., flow=0.25 ml/min, eluent phosphate buffer 50 mM pH 2.1/water/ACN=10/80/10 to 10/10/80 (v/v/v), run time=20 min.

Example 26 tert-Butyl 5-amino-2-(4-pyridyl)-4-(3-((N,N-bis-(2-methoxyethyl)-glycinyl)-amino)-phenyl)-thieno[2,3-d]pyrimidine-6-carboxamide To a stirred solution of tert-butyl 5-amino-4-(3-(2-bromoacetamido)-phenyl)-2-(4-pyridyl)-thieno[2,3-d]pyrimidine-6-carboxamide (example 25h), 200 mg) in DCM (5 ml) was added bis-(2-methoxyethyl)-amine (300 mg). After stirring for 17 h at room temperature, the reaction mixture was diluted with DCM (100 ml), washed with aq. NaHCO$_3$ (1 M, 2×50 ml), dried (MgSO$_4$) and concentrated in vacuo. The residue was purified by HPLC using a Luna C-18 column with the following gradient: 0.1% aq. TFA+10% aq. ACN/ACN=90/10 to 10/90 (v/v) in 30 min. The title compound was then lyophilized from a mixture of 1,4-dioxane, 0.1% aq. TFA and water.

Yield: 170 mg (TFA-salt) MS-ESI: [M+H]$^+$=592.2 HPLC: $R_t$=12.02 min, column Luna C-18(2), 3 μm, 100×2.0 mm, detection UV=210 nm, oven temperature=40° C., flow=0.25 ml/min, eluent phosphate buffer 50 mM pH 2.1/water/ACN=10/80/10 to 10/10/80 (v/v/v), run time=20 min.

Example 27

CHO-LH and CHO-FSH In Vitro Bioactivity

LH agonistic activity of compounds were tested in Chinese Hamster Ovary (CHO) cells stably transfected with the human LH receptor and cotransfected with a cAMP responsive element (CRE)/promotor directing the expression of a firefly luciferase reporter gene. Binding of ligand to the Gs-coupled LH receptor will result in an increase of cAMP, which in turn will induce an increased transactivation of the luciferase reporter construct. The luciferase signal was quantified using a luminescence counter. For test compounds, $EC_{50}$ values (concentration of test compound causing half-maximal (50%) stimulation) were calculated. For that purpose the software program GraphPad PRISM, version 3.0 (GraphPad software Inc., San Diego) was used.

In a similar way FSH agonistic activity of compounds were tested in CHO cells transfected with the luciferase reporter gene and the human FSH receptor. Results are shown in Table 1.

In vivo bioactivity

To measure the in vivo activity of LH/FSH receptor agonistic compounds ovulation induction in immature mice were studied. In this assay immature female mice were primed with urinary FSH (Humegon 12.5 IU/animal). Approximately 48 hours later the animals were treated with a LH/FSH agonistic compound, the preparation of which is described in examples 1, 4, 9 and 17, at a dose-level of 50 mg/kg. The animals were killed 24 hours after LH/FSH agonist treatment and the number of ova in the oviduct was microscopically assessed. On average 10-15 animals were tested. The mean number of ova amounted 8 with the exception of the compound of example 17 (which was 0.4).

TABLE 1

| name | example | LH EC50 (M) | FSH EC50 (M) |
|---|---|---|---|
| tert-Butyl 5-amino-2-methylthio-4-(3-((N-methyl-N-(2-hydroxyethyl)-glycinyl)-amino)-phenyl)-thieno[2,3-d]pyrimidine-6-carboxamide | 1 | 2.73E−09 | 5.69E−08 |
| tert-Butyl 5-amino-2-methylthio-4-(3-((N-(1-hydroxy-2-methyl-prop-2-yl)-glycinyl)-amino)-phenyl)-thieno[2,3-d]pyrimidine-6-carboxamide | 2 | 5.42E−09 | 8.06E−07 |
| tert-Butyl 5-amino-2-methylthio-4-(3-((N-(methoxycarbonylmethyl)-glycinyl)-amino)-phenyl)-thieno[2,3-d]pyrimidine-6-carboxamide | 3 | 5.97E−09 | 1.44E−06 |
| tert-Butyl 5-amino-2-methylthio-4-(3-((N-ethyl-N-(2-methoxyethyl)-glycinyl)-amino)-phenyl)-thieno[2,3-d]pyrimidine-6-carboxamide | 4 | 7.00E−09 | 1.01E−07 |
| tert-Butyl 5-amino-2-methylthio-4-(3-((N-(R-1-methoxycarbonyl-2-methyl-prop-1-yl)-glycinyl)-amino)-phenyl)-thieno[2,3-d]pyrimidine-6-carboxamide | 5 | 9.63E−09 | 3.48E−07 |
| tert-Butyl 5-amino-2-methylthio-4-(3-((N,N-bis-(2-methoxyethyl)-glycinyl)-amino)-phenyl)-thieno[2,3-d]pyrimidine-6-carboxamide | 6 | 1.00E−08 | 1.18E−06 |
| tert-Butyl 5-amino-2-methylthio-4-(3-((2,3-dihydroxy-prop-1-yl)-glycinyl)-amino)-phenyl)-thieno[2,3-d]pyrimidine-6-carboxamide | 7 | 1.22E−08 | 1.13E−06 |
| tert-Butyl 5-amino-2-methylthio-4-(3-((1,3-dihydroxyprop-2-yl)-glycinyl)-amino)-phenyl)-thieno[2,3-d]pyrimidine-6-carboxamide | 8 | 2.64E−08 | 1.00E−06 |
| tert-Butyl 5-amino-2-phenyl-4-(3-((N-ethyl-N-(2-hydroxyethyl)-glycinyl)-amino)-phenyl)-thieno[2,3-d]pyrimidine-6-carboxamide | 9 | 4.82E−09 | 6.06E−07 |
| tert-Butyl 5-amino-2-phenyl-4-(3-(N-(methoxycarbonylmethyl)-gycinyl)-amino)-phenyl)-thieno[2,3-d]pyrimidine-6-carboxamide | 10 | 1.01E−08 | 2.48E−06 |
| tert-Butyl 5-amino-2-(2-furyl)-4-(3-((N-methyl-N-(2-hydroxyethyl)-glycinyl)-amino)-phenyl)-thieno[2,3-d]pyrimidine-6-carboxamide | 11 | 4.00E−09 | 6.16E−07 |
| tert-Butyl 5-amino-2-(2-furyl)-4-(3-(N-(1-hydroxy-2-methyl-prop-2-yl)-glycinyl)-amino)-phenyl)-thieno[2,3-d]pyrimidine-6-carboxamide | 12 | 1.18E−08 | 2.97E−06 |
| tert-Butyl 5-amino-2-(2-furyl)-4-(3-(N-(methoxycarbonylmethyl)-glycinyl)-amino)-phenyl)-thieno[2,3-d]pyrimidine-6-carboxamide | 13 | 1.21E−08 | 2.55E−06 |
| tert-Butyl 5-amino-2-(2-thienyl)-4-(3-((N-methyl-N-(2-hydroxyethyl)-glycinyl)-amino)-phenyl)-thieno[2,3-d]pyrimidine-6-carboxamide | 14 | 5.28E−09 | 1.44E−06 |

TABLE 1-continued

| name | example | LH EC50 (M) | FSH EC50 (M) |
| --- | --- | --- | --- |
| tert-Butyl 5-amino-2-(2-thienyl)-4-(3-((N-(methoxycarbonylmethyl)-glycinyl)-amino)-phenyl)-thieno[2,3-d]pyrimidine-6-carboxamide | 15 | 1.82E−08 | 3.21E−06 |
| tert-Butyl 5-amino-2-(2-thienyl)-4-(3-((N,N-di-(2-methoxyethyl)-glycinyl)-amino)-phenyl)-thieno[2,3-d]pyrimidine-6-carboxamide | 16 | 2.13E−08 | 6.81E−06 |
| tert-Butyl 5-amino-2-ethylamino-4-(3-((N-ethyl-N-(2-methoxyethyl)-glycinyl)-amino)-phenyl)-thieno[2,3-d]pyrimidine-6-carboxamide | 17 | 1.04E−08 | 1.25E−06 |
| tert-Butyl 5-amino-2-(N,N-dimethylamino)-4-(3-((N-methyl-N-(2-hydroxyethyl)-glycinyl)-amino)-phenyl)-thieno[2,3-d]pyrimidine-6-carboxamide | 18 | 1.45E−08 | 1.63E−06 |
| tert-Butyl 5-amino-2-ethylamino-4-(3-((N-(methoxycarbonylmethyl)-glycinyl)-amino)-phenyl)-thieno[2,3-d]pyrimidine-6-carboxamide | 19 | 2.29E−08 | 2.30E−06 |
| tert-Butyl 5-amino-2-isopropylamino-4-(3-((N-ethyl-N-(2-methoxyethyl)-glycinyl)-amino)-phenyl)-thieno[2,3-d]pyrimidine-6-carboxamide | 20 | 4.24E−08 | 2.95E−06 |
| tert-Butyl 5-amino-2-allylamino-4-(3-((N-(methoxycarbonylmethyl)-glycinyl)-amino)-phenyl)-thieno[2,3-d]pyrimidine-6-carboxamide | 21 | 5.70E−08 | 5.60E−07 |
| tert-Butyl 5-amino-2-methoxy-4-(3-((N-ethyl-N-(2-methoxyethyl)-glycinyl)-amino)-phenyl)-thieno[2,3-d]pyrimidine-6-carboxamide | 22 | 1.16E−08 | 9.53E−07 |
| tert-Butyl 5-amino-2-allyloxy-4-(3-((N-ethyl-N-(2-methoxyethyl)-glycinyl)-amino)-phenyl)-thieno[2,3-d]pyrimidine-6-carboxamide | 23 | 3.68E−08 | 1.74E−06 |
| tert-Butyl 5-amino-2-isopropoxy-4-(3-((N-ethyl-N-(2-methoxyethyl)-glycinyl)-amino)-phenyl)-thieno[2,3-d]pyrimidine-6-carboxamide | 24 | 7.82E−08 | 2.51E−06 |
| tert-Butyl 5-amino-2-(4-pyridyl)-4-(3-((N-(1-hydroxy-2-methyl-prop-2-yl)-glycinyl)-amino)-phenyl)-thieno[2,3-d]pyrimidine-6-carboxamide | 25 | 3.47E−08 | 4.00E−07 |
| tert-Butyl 5-amino-2-(4-pyridyl)-4-(3-((N,N-bis-(2-methoxyethyl)-glycinyl)-amino)-phenyl)-thieno[2,3-d]pyrimidine-6-carboxamide | 26 | 3.82E−08 | 1.23E−06 |

The invention claimed is:

1. A thieno[2,3-d]pyrimidine compound according to formula I,

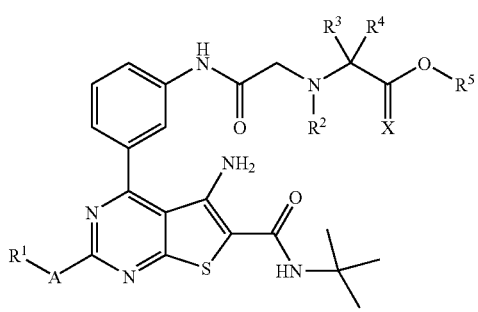

or a pharmaceutically acceptable salt thereof, wherein

X is O or H,H

A is S, NH, N($R^6$), O or a bond;

$R^1$ is (1-4C)alkyl, (2-4C)alkenyl, phenyl or (2-5C)heteroaryl, the phenyl or heteroaryl ring optionally being substituted with one or more of the group of substituents: hydroxy, halogen, nitro, trifluoromethyl, cyano, amino or (1-4C)(di)alkylamino;

$R^2$ is H, (1-4C)alkyl, (1-4C)alkoxy(2-4C)alkyl or hydroxy(2-4C)alkyl;

$R^3$ and $R^4$ can be independently selected from H, (1-4C)alkyl and hydroxy(1-4C)alkyl;

$R^5$ is H or (1-4C)alkyl, and $R^6$ can be selected from the same groups as described for $R^1$.

2. The compound according to claim 1, wherein X is H,H.

3. The compound according to claim 1, wherein $R^5$ is (1-4C)alkyl.

4. The compound according to claim 1, wherein $R^3$=$R^4$.

5. The compound according to claim 1, wherein $R^3$=$R^4$=H.

6. The compound according to claim 1, wherein $R^2$ is (1-4C)alkyl.

7. A pharmaceutical composition, comprising:
the thieno[2,3-d]pyrimidine compound according to claim 1 or a pharmaceutically acceptable salt thereof, and a pharmaceutically acceptable auxiliary.

8. A method to treat a fertility disorders in a patients in need of luteinizing hormone and follicle stimulating hormone agonistic treatment, comprising:
administering to the patient an effective amount of the compound or pharmaceutically acceptable salt thereof according to claim 1.

9. The method of claim 8, wherein the fertility disorder is selected from the group consisting of hypogonadism and male infertility.

10. The method of claim 8, wherein the fertility disorder is hypogonadism.

11. The method of claim 10, wherein the fertility disorder is male infertility.

12. A method for treating infertility in a woman in need of treatment by ovulation induction or by controlled hyperstimulation with a luteinizing hormone and follicle stimulating hormone agonist, the method comprising administering to the woman an effective amount of the compound or pharmaceutically acceptable salt thereof according to claim 1.

* * * * *

UNITED STATES PATENT AND TRADEMARK OFFICE
CERTIFICATE OF CORRECTION

PATENT NO.          : 7,375,109 B2                                       Page 1 of 1
APPLICATION NO.  : 10/488483
DATED                  : May 20, 2008
INVENTOR(S)        : Robert Gerardus Hannsen et al.

It is certified that error appears in the above-identified patent and that said Letters Patent is hereby corrected as shown below:

On the title page,

[*] Notice:    Subject to any disclaimer, the term of this patent is extended or adjusted under 35 USC 154(b) by (275) days Delete the phrase "by 275 days" and insert -- by 270 days --

Signed and Sealed this

Seventeenth Day of March, 2009

JOHN DOLL
*Acting Director of the United States Patent and Trademark Office*